(12) United States Patent
McKeon et al.

(10) Patent No.: US 11,642,426 B2
(45) Date of Patent: May 9, 2023

(54) ULTRAVIOLET SANITIZER WITH INDIVIDUALLY-CONTROLLED UV EMISSION INTERFACE CELLS

(71) Applicant: Nittany Solutions Group, LLC, Tequesta, FL (US)

(72) Inventors: Robert F. McKeon, Tequesta, FL (US); Scott A. Treser, Tequesta, FL (US)

(73) Assignee: Nittany Solutions Group, LLC, Tequesta, FL (US)

( * ) Notice: Subject to any disclaimer, the term of this patent is extended or adjusted under 35 U.S.C. 154(b) by 0 days.

(21) Appl. No.: 17/901,166

(22) Filed: Sep. 1, 2022

(65) Prior Publication Data

US 2022/0409757 A1 Dec. 29, 2022

Related U.S. Application Data

(63) Continuation-in-part of application No. 17/492,890, filed on Oct. 4, 2021, now Pat. No. 11,478,560, which is a continuation-in-part of application No. 17/074,015, filed on Oct. 19, 2020, now Pat. No. 11,246,470.

(60) Provisional application No. 63/138,029, filed on Jan. 15, 2021.

(51) Int. Cl.
*A61L 2/10* (2006.01)

(52) U.S. Cl.
CPC .............. *A61L 2/10* (2013.01); *A61L 2202/11* (2013.01); *A61L 2202/14* (2013.01)

(58) Field of Classification Search
None
See application file for complete search history.

(56) References Cited

U.S. PATENT DOCUMENTS

| | | | |
|---|---|---|---|
| 4,045,680 | A | 8/1977 | Loher |
| 6,614,039 | B2 | 9/2003 | Hollander |
| 7,511,283 | B2 | 3/2009 | Chor |
| 8,696,985 | B2 | 4/2014 | Gil et al. |
| 10,064,966 | B2 | 9/2018 | Kassel et al. |

(Continued)

FOREIGN PATENT DOCUMENTS

| | | |
|---|---|---|
| CA | 2937695 A1 | 5/2015 |
| KR | 20170007245 A | 1/2017 |

*Primary Examiner* — Natasha N Campbell
*Assistant Examiner* — Pradhuman Parihar
(74) *Attorney, Agent, or Firm* — Burns & Levinson LLP; Christopher Carroll

(57) ABSTRACT

A UV sanitizing device including a sanitizing interface having a top surface arranged to support a device positioned above the sanitizing interface where the sanitizing interface includes a translucent material arranged to allow UV light to pass through An adjustable UV emission interface, positioned adjacent to the sanitizing interface, arranged to adjustably conform to the shape of a device facing the sanitizing interface, and arranged to emit the UV light toward the sanitizing interface in the shape of the device. The adjustable UV emission interface includes UV emission interface cells such that, when a first portion of the UV emission interface cells is activated and a second portion of the UV emission interface cells is deactivated, the UV emission interface conforms to the shape of the device. Each cell of UV emission interface cells includes a sensor arranged to detect a portion of the device facing the sanitizing interface.

10 Claims, 31 Drawing Sheets

(56) References Cited

U.S. PATENT DOCUMENTS

| | | | |
|---|---|---|---|
| 10,702,126 B2 | 7/2020 | Desu-Kalyanam | |
| 2010/0193709 A1* | 8/2010 | Dalton | A61L 2/10 250/504 R |
| 2011/0252585 A1 | 10/2011 | Lee | |
| 2014/0170019 A1 | 6/2014 | Gil et al. | |
| 2017/0035918 A1 | 2/2017 | Kassel et al. | |
| 2018/0126019 A1* | 5/2018 | Prieto Andreu | A61L 2/10 |
| 2018/0154032 A1 | 6/2018 | Dombrowsky et al. | |
| 2020/0078483 A1* | 3/2020 | Eidman | A47L 23/263 |

* cited by examiner

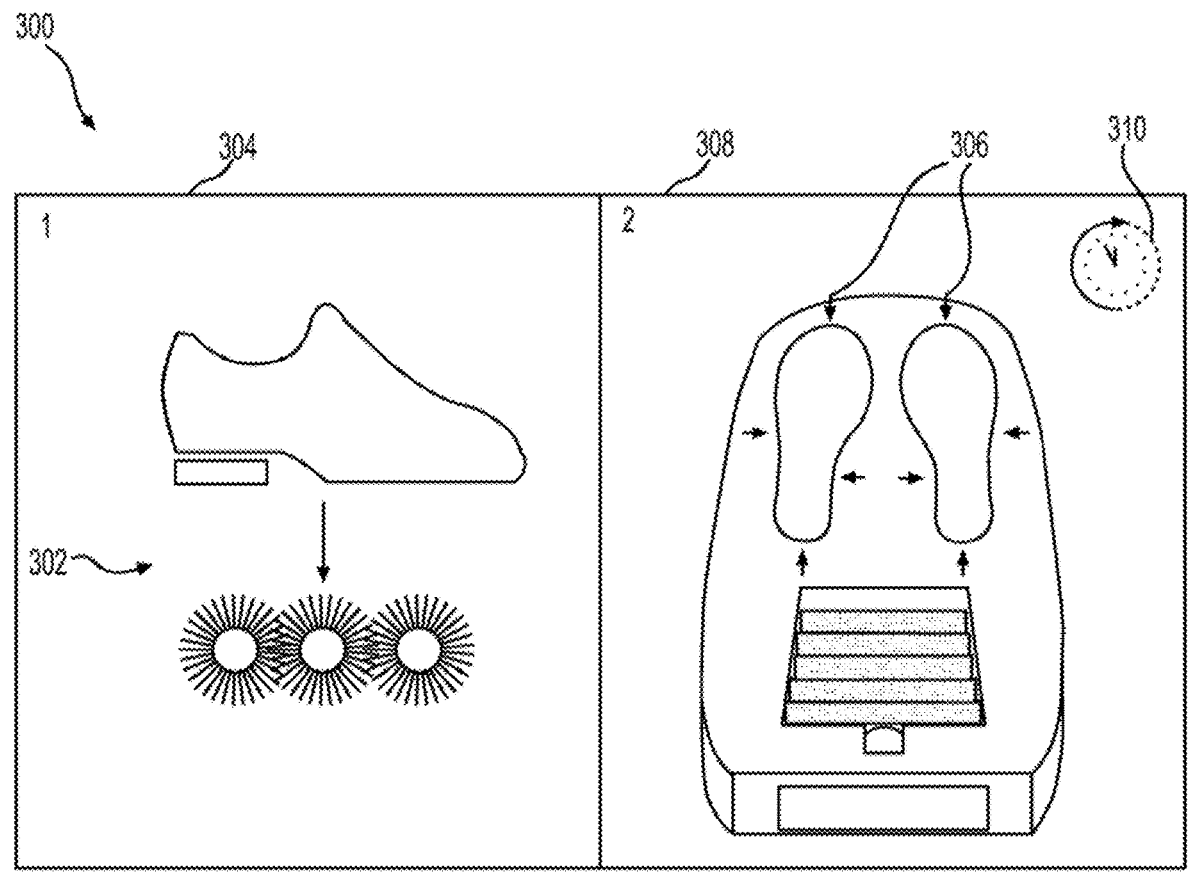
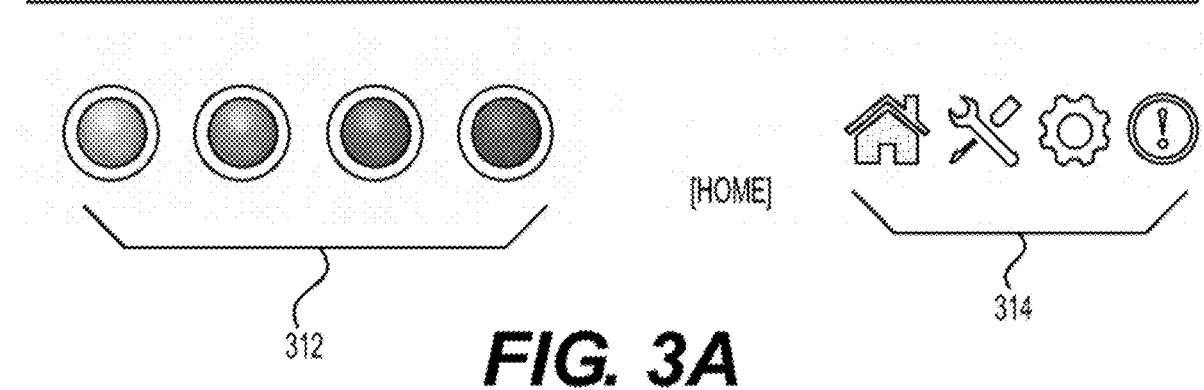
FIG. 3A

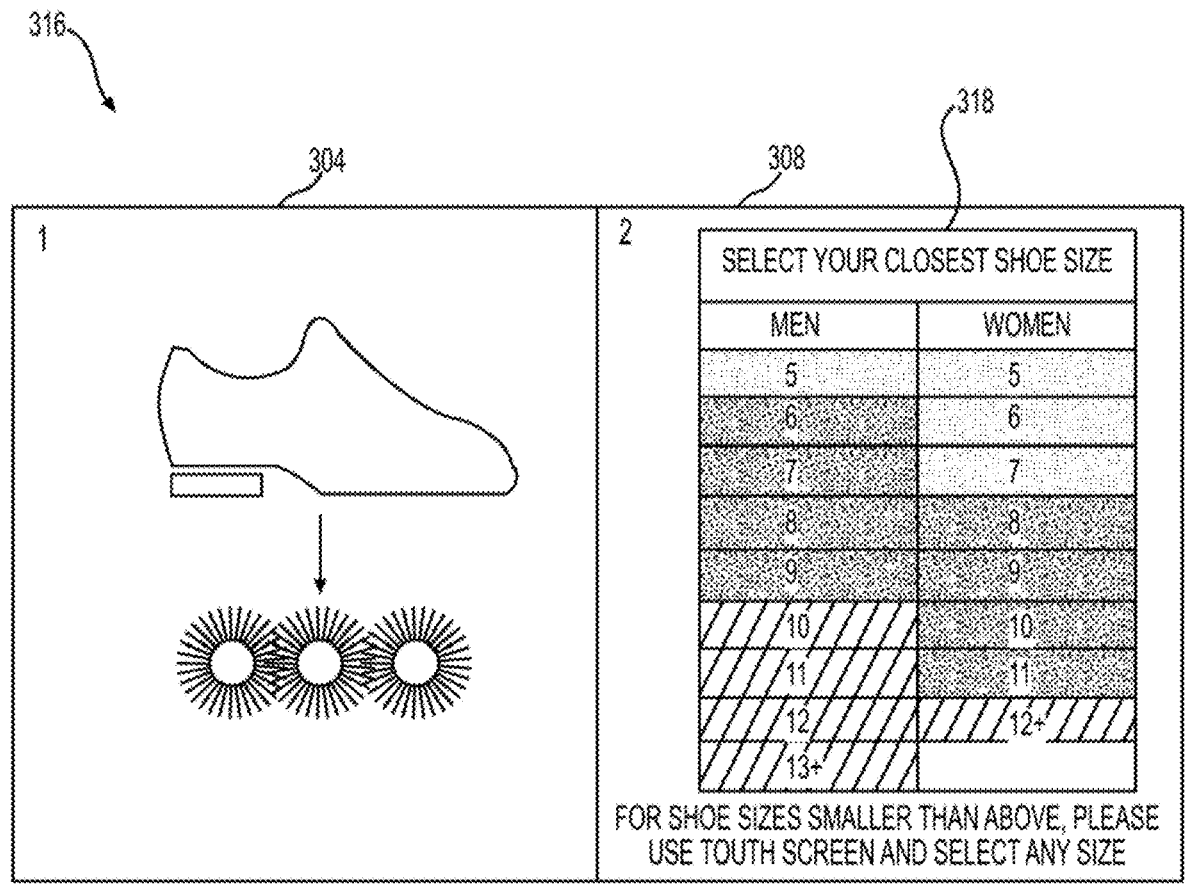
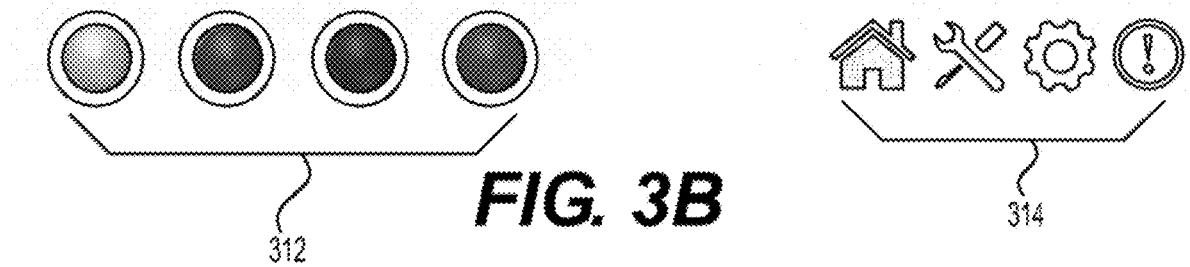
FIG. 3B

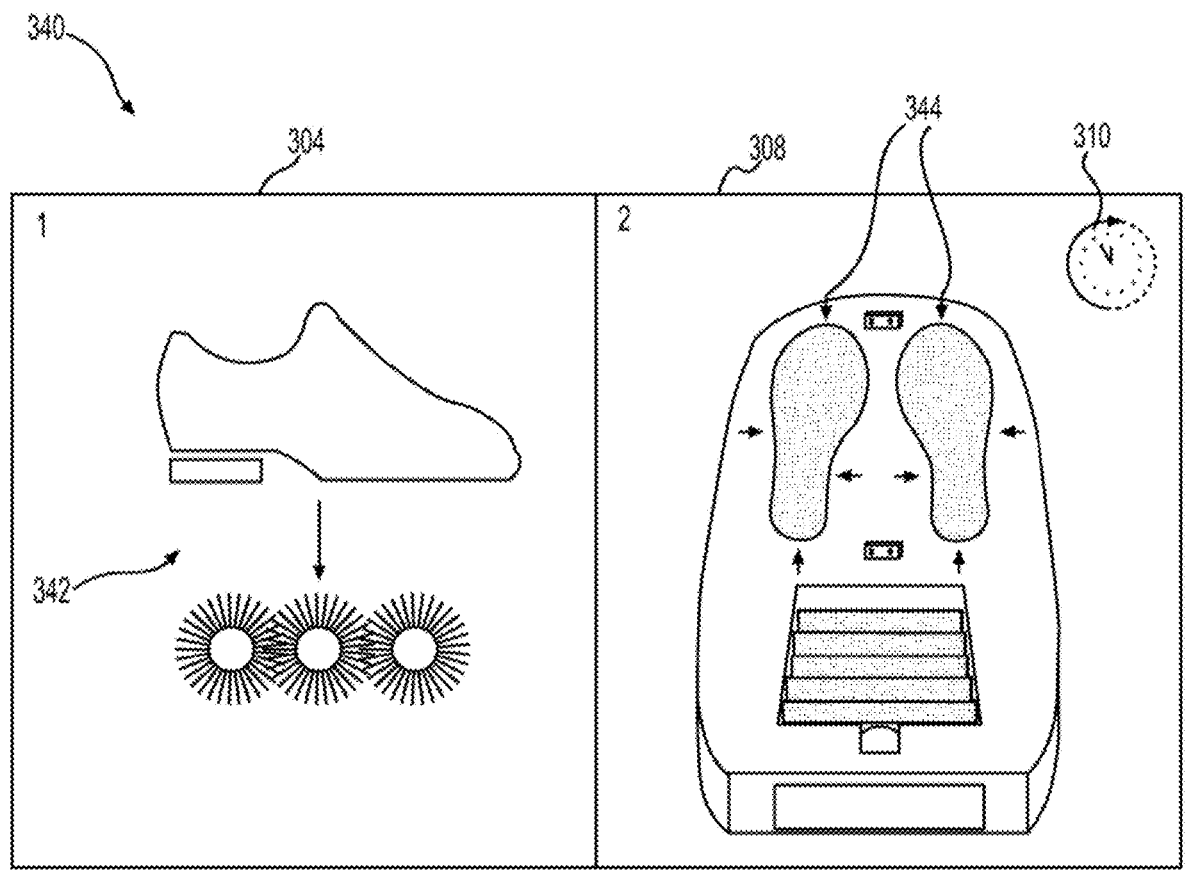
FIG. 3D

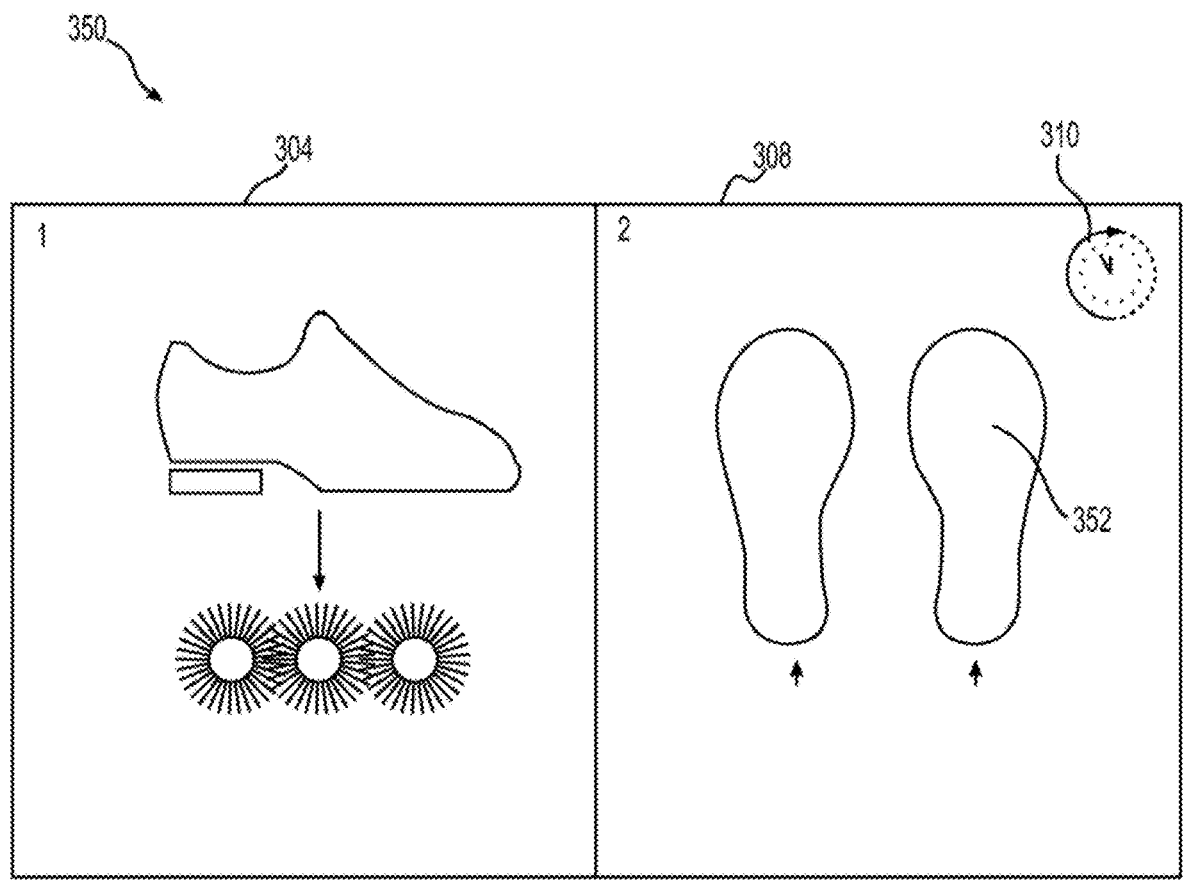
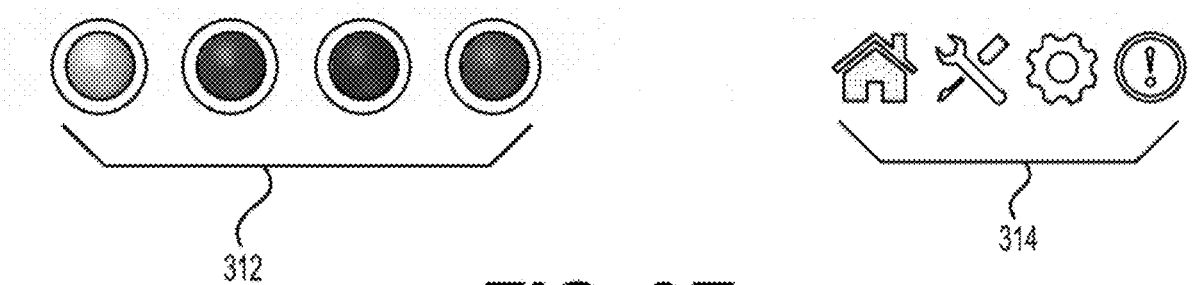
FIG. 3E

360 — TROUBLE SHOOTING

362

| LED COLOR | | | | SYMPTOM | SOLUTION |
|---|---|---|---|---|---|
| AMBER | RED | BLUE | GREEN | | |
| SOLID | SOLID | OFF | OFF | SYSTEM DID NOT COMPLETE | GET OFF OF MACHINE AND RESTART CLEANING PROCEDURE |
| SOLID | SINGLE BLINK EVERY 2 SECONDS | | | MOTOR PROBLEM | ENSURE THAT NOTHING IS JAMMED IN THE BRUSHES. REFER TO... |
| SOLID | DOUBLE BLINK EVERY 2 SECONDS | | | UV LIGHT PROBLEM | REPLACE UV-C BULB WITH A NEW ONE. SEE INSTRUCTION MANUAL: REPLACEMENT PARTS |
| SOLID | TRIPLE BLINK EVERY 2 SECONDS | | | OVERHEAT | UNPLUG THE UNIT. ENSURE THAT THE MACHINE HAS ADEQUATE VENTILATION AND THAT NOTHING IS BLOCKING PROPER AIR FLOW FROM ALL SIDES |
| SOLID | RED/BLUE/GREEN ALTERNATE BLINK EVERY SECOND | | | FILTER NEEDS CLEANED (FILTER?) | EMPTY DEBRIS CONTAINER... |

SETTINGS

382

| ITEM | DEFAULT SETTING | | | | | |
|---|---|---|---|---|---|---|
| LANGUAGE | ENGLISH | SPANISH | GERMAN | FRENCH | ITALIAN | |
| SANITIZING DURATION | 10 SECONDS | 20 SECONDS | 30 SECONDS | 60 SECONDS | 90 SECONDS | 180 SECONDS |
| EMPTY DEBRIS TRAY REMINDER FREQUENCY | DAILY | EVERY OTHER DAY | TWICE PER WEEK | WEEKLY | EVERY OTHER WEEK | MONTHLY |

[SETTINGS]

314

| SOLE CLEANER SPECIFICATION SHEET | | | | |
|---|---|---|---|---|
| PROPERTY/ITEM | INCLUDED | NOT INCLUDED | PARAMETER VALUES/ SETTING | NOTES |
| DIMENSIONS | | | | |
| PLATFORM DIMENSIONS | | | | |
| HEIGHT (H): | | | 3" TO 4" | PREFERABLY AS LOW AS POSSIBLE |
| WIDTH (W): | | | 13" - 17" | AS NEEDED |
| DEPTH (D): | | | 24"-28" | AS NEEDED |
| OVERALL DIMENSIONS | | | | |
| HEIGHT (H): | | | 36" TO 40" | ADJUSTABLE IN SOME IMPLEMENTATIONS |
| WIDTH (W): | | | 13" - 17" | AS NEEDED |
| DEPTH (D): | | | 24"-28" | AS NEEDED |
| WEIGHT (WITH HANDLE / WITHOUT HANDLE) | | | 40 LBS / 35 LBS? | ESTIMATED GOAL |
| ELECTRICAL | | | | |
| SUPPLY VOLTAGE | X | | 120 VAC, 50/60 HZ | |
| TOTAL AMPERAGE DRAW | X | | < 10 AMPS | |
| UV EMITTER MODEL & SPECIFICATION | X | | LENGTH, WAVELENGTH (~260 NM), WATTAGE | |
| MOTOR FOR BRUSHES | X | | TBD | AS SPECIFIED |
| MAIN POWER CORD, 12GA, GROUNDED | X | | | AS SPECIFIED |

| INPUTS | | | |
|---|---|---|---|
| POWER ON/OFF SWITCH (MAIN) | X | TOGGLE SWITCH ON BASE | |
| THERMOSTAT (SNAP DISC TYPE, THERMAL) | X | | TEMPERATURE SENSOR, TO BE SPECIFIED |
| MOTION / PRESSURE SENSOR, BRUSH ACTUATION | X | | SENSOR SPECIFICATION |
| MOTION / PRESSURE SENSOR, UV LIGHT ACUATION | X | | SENSOR SPECIFICATION |
| SANITIZING DURATION SELECTION | X | 3 CHOICES: 10, 20, 30 SECONDS | SANITIZATION EFFECTIVENESS MUST CORRESPOND WITH MARKETING/ OPERATION MANUAL CLAIMS |
| EMERGENCY STOP (E-STOP) SWITCH | X | ON/OFF | LOCATE ON SUPPORT HANDLE IN ONE CONFIGURATION |
| OUTPUTS | | | |
| LED INDICATION (POWER ON) | X | AMBER SOLID | |
| LED INDICATION (DEBRIS CLEANING TO OCCUR) | X | AMBER SOLID, GREEN BLINK RAPIDLY | |
| LED INDICATION DEBRIS CLEANING (BRUSHES ON) | X | AMBER SOLID, GREEN BLINK EVERY 1 SECOND | |
| LED INDICATION (UV CLEANING TO OCCUR) | X | AMBER SOLID, GREEN SOLID, BLUE BLINK RAPIDLY | |
| LED INDICATION (UV CLEANING) | X | AMBER SOLID, GREEN SOLID, BLUE BLINK EVERY 1 SECOND | |
| LED INDICATION (COMPLETE) | X | AMBER SOLID, GREEN SOLID, BLUE SOLID | |
| LED INDICATION (SERVICE REQUIRED) | X | AMBER SOLID, RED SOLID | SYSTEM DID NOT COMPLETE |
| LED INDICATION (SERVICE REQUIRED) | X | AMBER SOLID, RED BLINK EVERY 2 SECONDS | MOTOR PROBLEM |
| LED INDICATION (SERVICE REQUIRED) | X | AMBER SOLID, RED DOUBLE BLINK EVERY 2 SECONDS | UV LIGHT PROBLEM |
| LED INDICATION (SERVICE REQUIRED) | X | AMBER SOLID, RED BLINK EVERY 1/2 SECONDS | OVERHEAT |
| LED INDICATION (SERVICE REQUIRED) | X | AMBER SOLID, RED/BLUE/GREEN ALTERNATE BLINK EVERY SECOND | FILTER MAY NEED CLEANING |
| LED INDICATION (POWER OFF) | X | NO LED INDICATION | POWER SWITCH IS TOGGLED OFF OR UNIT IS UNPLUGGED |
| CORRESPONDING AUDIBLE BEEPING FEEDBACK | X | IS THIS FEATURE NEEDED IN ADDITION TO THE VISUAL INDICATIONS? | |

*FIG. 6B*

↓ FROM FIG. 6B

| MATERIALS | | | | |
|---|---|---|---|---|
| BASE, INTERNAL FRAME | X | | GALVANIZED STEEL, 12/14/16 GAGE, AS NEEDED | FINALIZE SPEC |
| BASE, EXTERNAL SHELL | X | | FRP, SATIN/FLAT/GLOSS WHITE | FINALIZE SPEC |
| EXTENSION HANDLE, CORE | X | | MAY BE GALVANIZED TUBING | FINALIZE SPEC |
| EXTENSION HANDLE, SHELL | X | | FRP, SATIN/FLAT/GLOSS WHITE | FINALIZE SPEC |
| DEBRIS FILTER OR REMOVABLE TRAY? | X | X | | |
| SUPPORT FEET (2 OR 4?) | X | X | FOR STABILITY. MAY BE ADJUSTABLE. | FINALIZE SPEC |
| ROLLER WHEELS (2) | X | X | FOR PORTABILITY. MAY RETRACT. | FINALIZE SPEC |
| THIRD PARTY APPROVALS | | | | |
| UL, cUL | X | X | ORDINARY AREA, RESIDENTIAL USE ONLY | |
| CE, FM, ETL? | X | X | | |
| OPTIONS | | | | |
| SMART CAPABLE | | X | | NEXT GENERATION OPTION |
| FLOOR MOUNTING | | X | | |
| WALL MOUNTING | | X | | |
| ADD PHONE SANITIZATION FEATURE? | | X | | |
| ADD PHONE CHARGING FEATURE. | | X | | |

*FIG. 6C*

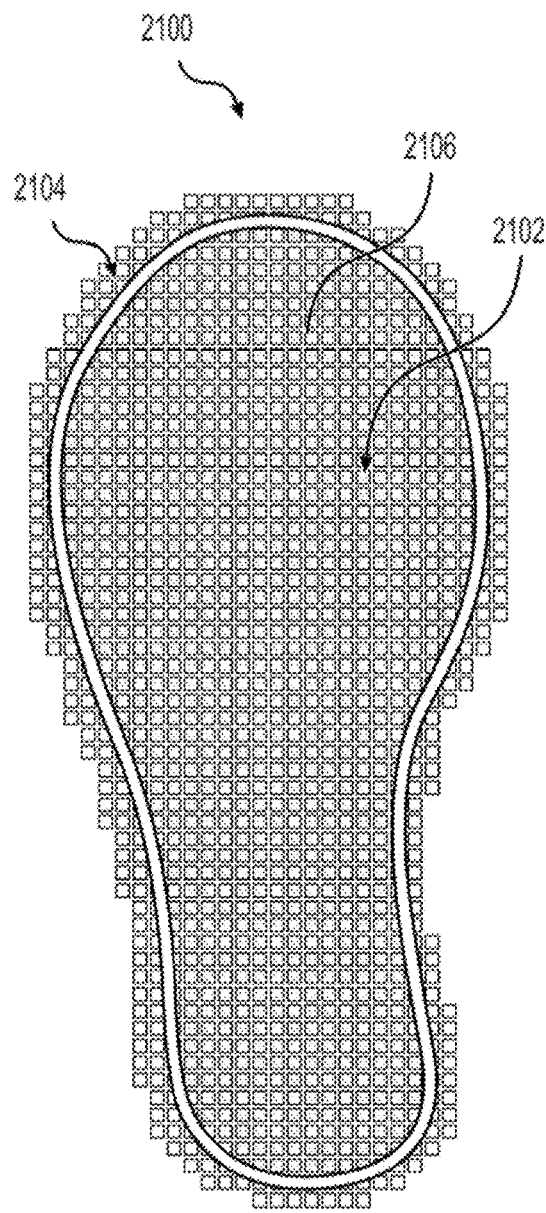
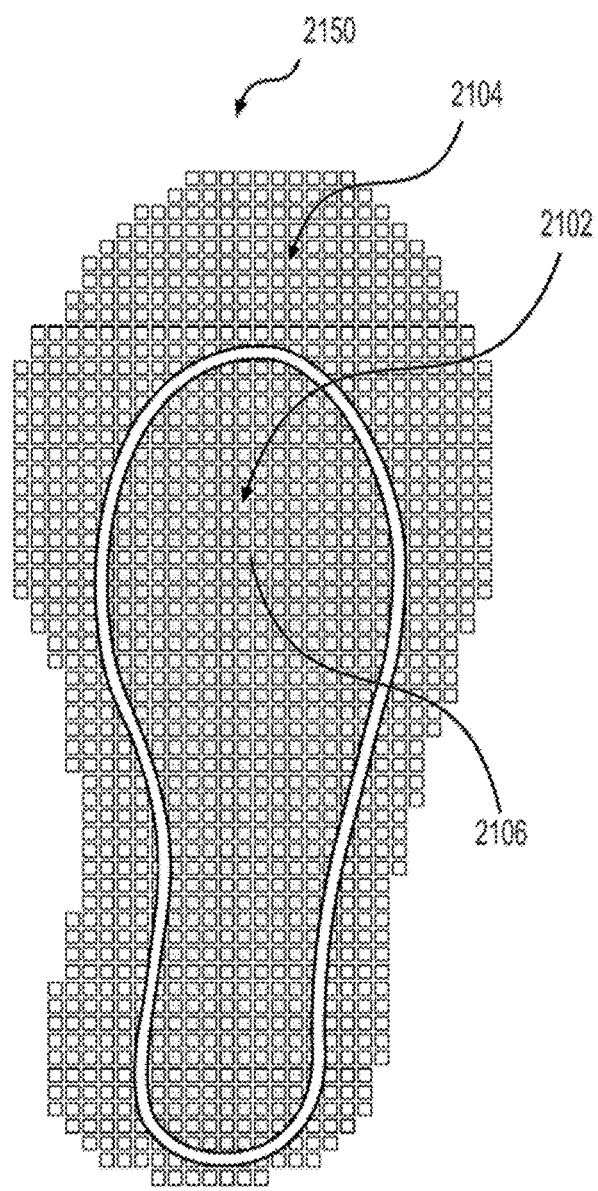
FIG. 15A  FIG. 15B

ULTRAVIOLET SANITIZER WITH INDIVIDUALLY-CONTROLLED UV EMISSION INTERFACE CELLS

REFERENCE TO RELATED APPLICATIONS

This application is a continuation-in-part of U.S. patent application Ser. No. 17/492,890, filed on Oct. 4, 2021, which issued as U.S. Pat. No. 11,468,560, which is a continuation-in-part of U.S. patent application Ser. No. 17/074,015, filed on Oct. 19, 2020, which issued as U.S. Pat. No. 11,246,470. U.S. patent application Ser. No. 17/492,890 claims priority to and the benefit of U.S. Provisional Patent Application No. 63/138,029, filed on Jan. 15, 2021, entitled "Infinite Ultraviolet Shielding Devices, Systems, and Methods." The entire contents of the above-referenced patent applications are incorporated herein by reference.

TECHNICAL FIELD

This application relates generally to device sanitization techniques and, more particularly, to ultraviolet sanitizing techniques.

BACKGROUND

Biocontamination, including the spread of bacteria and viruses, has traditionally been a threat to humans and animals. Bacteria, viruses, and other microorganisms that can cause serious illness or infectious diseases are typically spread by persons walking into contaminated areas and then transporting the contaminants to other areas via the soles of their footwear. Such contaminants are then typically deposited from the soles of a person's footwear to previously uncontaminated floor surfaces from which these contaminants further spread to the soles of other persons walking on the floor surfaces. This cycle can continue until contaminants are spread throughout a building or buildings as persons' with contaminated soles move from place to place.

Eventually some persons will touch the soles of their shoes or floor surfaces, or contaminants can become airborne, resulting in dangerous exposures to anyone within contaminated areas. Hospitals, other healthcare facilities, or facilities having a high density of people are especially vulnerable to contaminants due to a significantly increased possibility that persons will be exposed to harmful bacteria, viruses, and other microorganisms. Biocontaminants have spread from the soles of contaminated shoes to various types of floor surfaces including cement floors, wood floors, and carpeted floors, which are often subsequently picked up directly by persons in contact with such floor surfaces or indirectly via their footwear soles.

Shoe sole cleaning, such as in residential environments, is largely limited to manual debris removal via outdoor and indoor floor mats, which are typically located in close proximity to main entryways. These devices provide varying levels of debris removal from shoe soles. Due to their inherent design, they are incapable of removing or eliminating disease-causing microscopic organisms and bio-contaminants such as bacteria, viruses, and other harmful germs and spores from the shoe sole.

There are existing systems that provide for the reduction of pathogens from the soles of shoes. However, these systems do not adequately prevent re-contamination of footwear soles after the decontamination process. Also, current systems provide minimal to no ultraviolet (UV) light shielding to users during the decontamination process. Hence, there is a need to more effectively and safely reduce or eliminate the likelihood of spreading bio-contaminants via the footwear soles of persons moving from place to place, while protecting individual users from potentially harmful UV rays. Aside from footwear, other devices are often exposed to contamination such as articles of clothing, handheld or user operated equipment, mobile devices, wearable items (e.g., jewelry), and vehicles. Unfortunately, existing systems that provide decontamination of the other types of devices either provide inadequate UV protection to users or are cumbersome to use.

Furthermore, UV-C light, at several peak wavelengths between 200 nm and 280 nm, has been proven to be highly effective and efficient in the sanitization of pathogens when properly exposed to surfaces and fluids in residential, commercial, and industrial applications. Unfortunately, direct exposure of UV-C light in these wavelengths can be extremely harmful to human skin and eyes.

Conventional UV-C sanitizing applications are typically executed while humans are isolated from the harmful UV-C rays or when they are not present. However, studies have shown that humans and human devices are transporters of pathogens into and within facilities. Therefore, for many establishments, the inability to sanitize owners, patrons, vendors, and workers, or their personal belongings or devices, is undesirable.

Hence, there exists a need to provide enhanced pathogen sanitizing functions for devices, which utilize UV-C light, whereby human presence should not be a concern. This would effectively reduce the transportation of pathogens into and throughout residential, commercial, and industrial facilities, and therefore improve the overall health and safety in these establishments.

SUMMARY

The application, in various implementations, addresses deficiencies associated with cleaning and sanitizing devices used by humans.

This application describes exemplary systems, methods, and devices that effectively remove and collect debris from various types of devices including, but not limited to footwear soles, and also effectively sanitize any side of a device or bottom of footwear (also referred to herein as a "sole" or "soles"). A device may include, without limitation, an article of clothing, handheld equipment, user-operated equipment, a mobile device, computer, electronic consumer device, firearms, wearable items (e.g., jewelry), a tent, a protective suit, a vehicle, an autonomous vehicle, an autonomous ariel vehicle (AAV), and so on. Footwear may include, without limitation, shoes, sneakers, sandals, slippers, boots, and any type of foot apparel worn by users to protect their feet. The exemplary cleaning and sanitizing techniques described herein create a cleaner and healthier environment in daily living, recreational, and/or working areas. The exemplary systems, methods, and devices also incorporate techniques for screening a user from any UV light that goes beyond or escapes past the user's device including, without limitation, deploying a UV shield and/or controlling UV light emissions such that UV light is only emitted when a user's device is determined to be in a designated position.

In some implementations, the inventive systems, methods and devices herein provide a fully integrated debris removal stage with a pathogen and/or contaminant sanitization stage. Such a two-stage process and/or sequence is advantageous because debris collected on a portion of a device, e.g., footwear soles or mobile phone body, that may compromise or inhibit effective sanitization of the device is removed before the sanitization stage to eliminate any physical or line-of-sight barrier between a UV emitter and contaminants and/or pathogens on a device, e.g., a footwear sole.

The Centers for Disease Control and Prevention (CDC) and independent hospital reports claim that pathogens are commonly transported by devices, such as footwear, from one area to another. In various implementations, the systems, methods, and devices described herein promote a forward directional or one-way travel path having an entrance and an exit for the user to move through the footwear sole cleaning and sanitization process. This advantageously eliminates the possibility that users will re-contaminate their footwear soles by back-tracking their steps directly into the path of all previous users.

In certain implementations, the present disclosure includes a "digital" shield system that protects users in close proximity to equipment that utilizes UV-C light during sanitizing applications. Such devices, systems, and/or methods accurately generate a 2-dimensional screen shape or shapes that precisely matches the outline of a sensed object that is in close proximity. The screen safely blocks the user from the UV-C light that is outside of the assumed shape or shapes while also allowing proper exposure of UV-C light to the assumed shape or shapes. In certain configurations, the screen can assume any one of a plurality of shapes, i.e., assume an infinite 2-dimensional shape form capability within a defined space.

In further implementations, the present disclosure includes a UV sanitizes device and/or system having multiple individually-controlled and/or independently-controlled and/or autonomous UV emission interface cells capable of individually detecting the presence of a device aligned with each cell and, in response, activating one or more UV light emitters included in an individual cell. Each independently-controlled cell may employs at least one resistor, transistor, phototransistor, and LED emitter (capable of transmitting light within the Germicidal UVC frequency band, or wavelengths between 200 to 280 nanometers). The phototransistor may control the actuation of at least one UVC LED emitter. The resistors and transistors may provide biasing and/or stabilize the sensitivity of the phototransistor. The cells may be arranged in an array such that each cell that is not on the perimeter of the array is in contact with (adjacent to) four other cells or in the center of eight cells. Perimeter cells will have a least one less cell adjacent to it. Each cell size may be less than or equal to about ⅟₆₄"×⅟₆₄", ⅟₃₂"×⅟₃₂" ⅟₁₆"×⅟₁₆", ⅛"×⅛", ¼"×¼", ½"×½", 1"×1", 5"×5", 10"×10", 1'×1', 5'×5', and 10'×10'.

In one aspect, a UV sanitizing device includes a sanitizing interface having a top surface arranged to support a device positioned above the sanitizing interface where the sanitizing interface includes a translucent material arranged to allow UV light to pass through. The UV sanitizing device also includes an adjustable UV emission interface, positioned adjacent to the sanitizing interface, that is arranged to adjustably conform to the shape of a surface of the device facing the sanitizing interface, and arranged to emit the UV light toward the sanitizing interface in the shape of the surface of the device. The adjustable UV emission interface includes a plurality of UV emission interface cells such that, when a first portion of the UV emission interface cells is activated and a second portion of the UV emission interface cells is deactivated, the UV emission interface conforms to the shape of the surface of the device. Each cell of the plurality of UV emission interface cells includes a sensor arranged to detect a portion of the surface of the device facing the sanitizing interface.

Each cell of the plurality of UV emission interface cells may include at least one UV light emitter arranged to emit a portion of the UV light toward the device and through the sanitizing interface when activated. Each cell of the plurality of UV emission interface cells may be individually controllable by an activator circuit. The activator circuit may activate the at least one UV light emitter in response to its respective sensor determining that the portion of the surface of the device facing the sanitizing interface is aligned with its respective sensor along an axis extending from the respective UV emission interface cell toward the portion of the surface of the device facing the sanitizing interface.

The sensor may include a photo-reactive device. The photo-reactive device may include a phototransistor. The phototransistor may determine that the portion of the surface of the device facing the sanitizing interface is aligned with the phototransistor by detecting a change in light intensity received by the phototransistor. The sensor may include at least one of a photo-reactive device, an acoustic sensor, a sonic sensor, a capacitance sensor, a pressure sensor, a mass sensor, and a magnetic sensor.

The plurality of UV emission interface cells may be configured as an array of UV light emitters arranged to selectively activate the first portion of the UV emission interface cells and deactivate the second portion of the UV emission interface cells to emit the UV light toward the surface of device. The at least one UV light emitter in each of the plurality of the UV emission interface cells may include an LED emitter. The UV sanitizing device may include a proximity sensor arranged to detect the presence of the device when positioned above the sanitizing interface.

In another aspect, a UV emission interface cell includes a sensor arranged to detect an object along an axis extending from the sensor. The cell also includes at least one UV light emitter arranged to emit UV light toward the object. The cell further includes an activator circuit arranged to activate the at least one UV light emitter in response to the sensor detecting that the object is aligned along the axis extending from the sensor.

The activator circuit may be further arranged to deactivate the at least one UV light emitter in response to the sensor determining that the object is not aligned along the axis extending from the sensor. The phototransistor may be arranged to determine when the object is aligned with the phototransistor by detecting a change in light intensity received by the phototransistor. The phototransistor may be arranged to determine when the light intensity decreases below a level indicating that the object is aligned along the axis extending from the phototransistor. The detected object may be a portion of a device. The planar size of the cell may be less than or equal to 0.015624 in².

The activator circuit may include an activator capacitor electrically coupled in parallel with the at least one UV light emitter and arranged to discharge an electrical current to the at least one UV light emitter while the at least one UV light emitter is activated.

In a further aspect, a method for manufacturing a UV emission interface cell includes: providing a sensor arranged to detect an object along an axis extending from the sensor; providing at least one UV light emitter arranged to emit UV light toward the object; and electronically coupling an activator circuit to the sensor and the at least one UV light emitter, the activator circuit arranged to activate the at least one UV light emitter in response to the sensor detecting that the object is aligned along the axis extending from the sensor.

Any two or more of the features described in this specification, including in this summary section, may be combined to form implementations not specifically described in this specification. Furthermore, while this specification may refer to examples of systems, methods, and devices related to devices for humans, such techniques also apply equally to cleaning and sanitizing devices associated with animals.

The details of one or more implementations are set forth in the accompanying drawings and the following description. Other features and advantages will be apparent from the description and drawings, and from the claims.

DESCRIPTION OF THE DRAWINGS

FIGS. 3A-3G show a series of user interface screen shots displayed to a user as they operate the exemplary sole debris cleaning and sanitization systems of FIGS. 1 and 4;

FIGS. 6A, 6B, and 6C show a specification table for an exemplary configuration of a debris cleaning and sanitization device;

FIGS. 15A and 15B are top-down views of a UV sanitizing device showing a portion of cells that are open and portion of cells that are closed depending on the shape of detected footwear or a portion of UV light emitter cells that are activated and portion of UV light emitter cells that are not activated depending on the shape of the detected footwear;

Like reference numerals in different figures indicate like elements.

DETAILED DESCRIPTION

The application, in various implementations, addresses deficiencies associated with cleaning and sanitizing devices used by humans or animals. This application describes exemplary systems, methods, and devices that effectively remove and collect debris from devices and also effectively sanitize a portion of the devices including, for example, the bottoms and/or soles of footwear. The exemplary cleaning and sanitizing techniques described herein create a cleaner and healthier environment in daily living, recreational, and/or working areas. The exemplary systems, methods, and devices also incorporate techniques for screening a user from any UV light that goes beyond or escapes past the user's device including, without limitation, deploying a UV shield and/or controlling UV light emissions such that UV light is only emitted when a user's device is determined to be in a designated position.

Figure 1:
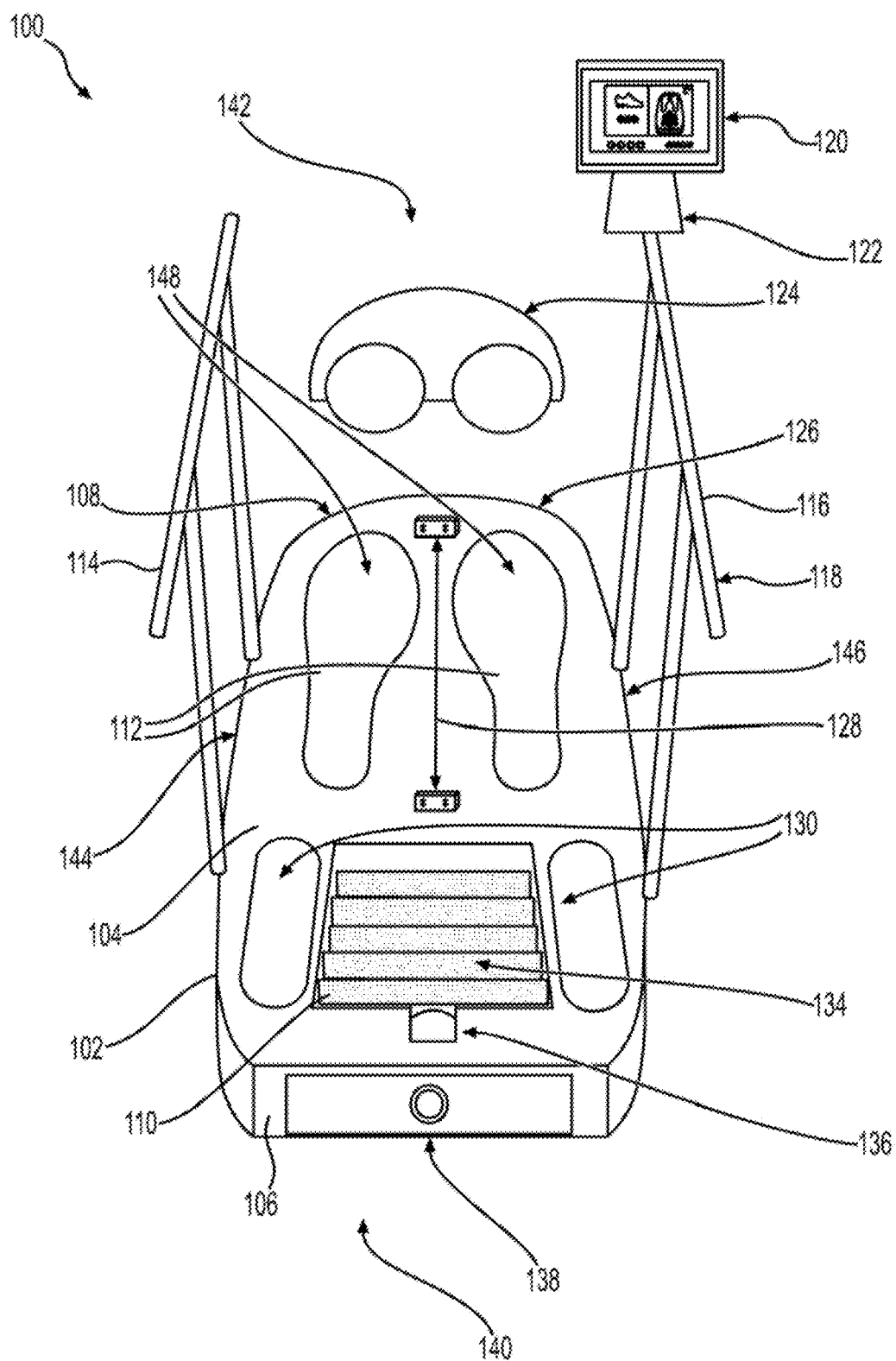
FIG. 1 is a diagram of an exemplary sole debris cleaning and sanitization system and/or device.

FIG. 1 is a diagram of an exemplary sole debris cleaning and sanitization system and/or device 100 including a debris cleaner 134 and sanitizer 148 within housing 102. Housing 102 includes a top surface 104, a first side 106 that is adjacent to a user entry portal 140, and a second side 108 that is adjacent to a user exit portal 142. A first railing 114 and second railing 116 extend along sides 144 and 146 respectively and may be mounted on top surface 104. In some implementations, only one railing such as railing 116 is mounted on top surface 104.

Railing 116 may include one or more rails such as rail 118 that may extend horizontally or vertically to form railing 116. In one configuration, railings 114 and 116 define a pathway through which a user passes along from user entry portal 140 to user exit portal 142. Railing 114 and/or 116 may provide hand holding rails such as rail 118 to allow a user to support themselves while moving along the pathway or provide support while moving their feet to various positions along top surface 104. Debris remover 134 may have one or more debris removal elements, e.g., brushes, extending toward a debris removal opening 110 in top surface 104. The brushes may be arranged to contact the footwear sole of a user while the footwear sole is positioned over the debris removal opening 110 and remove debris from the footwear sole.

In one implementation, the debris removal opening 110 is in proximity or substantially adjacent to the first side 106 and/or user entry port 140. Stepping areas 130 may provide locations where a user can place one shoe while contacting their other shoe with the brushes of debris remover 134 or place both shoes before or after the debris removal brushes are rotated to remove debris from footwear soles. In one implementation, the brushes of debris remover 134 are stationary, requiring a user to move the footwear against the brushes in an abrasive manner to remove debris on the footwear soles.

Sanitizer 148 may have one or more sanitizing elements, e.g., a UV emitter that emits UV light, directed toward one or more sanitizing interfaces 112 on top surface 104. The UV emitter or emitters may include one or more UV-LEDs (e.g., Mini-LEDs or Micro-LEDs) and/or UV mercury lamps. The emitted UV light and/or rays may include wavelengths from about 100 to 380 nm. The UV emitter or emitters may include at least one of a UV-A emitter (e.g., emitting UV light having about 320 to 400 nm wavelengths), a UV-B emitter (e.g., emitting UV light having about 280 to 320 nm wavelengths), and a UV-C emitter (e.g., emitting UV light having about 200 to 280 nm). The sanitizing elements will be substantially aligned with a footwear sole while the footwear sole is positioned over the one or more sanitizing interfaces 112 to remove contaminants from the footwear sole. In one implementation, the one or more sanitizing interfaces 112 are positioned laterally on top surface 104 between debris removal opening 110 and the second side 108 and/or user exit portal 142 of the housing 102. Sanitizing interfaces 112 may include a transparent, semi-transparent, or translucent material that passes through UV light emitted from the one or more UV emitters toward a footwear sole or soles positioned over one or more sanitizing interfaces 112. A sanitizing interface may include glass, plexiglass, plastic, grates, and/or a material configured to allow UV light to pass through. The one or more sanitizing interfaces 112 may reside within and/or define one or more sanitization areas. The sanitization areas may be shaped to form an outline of, for example, shoes or other footwear as illustrated in FIG. 1. Top surface 104 may include a stop area 136 to accommodate high-heeled shoes.

Housing 102 may include one or more sensors 128 arranged to generate sensor data based on a detected position of a footwear sole, detected position of a user, detected temperature of a component of system 100, detected presence of debris on a footwear sole, and/or a detected presence of a contaminant on a footwear sole. In one implementation, sensors 128 are arranged to detect the presence and/or position of footwear soles within the sanitization areas defined by sanitization interfaces 112. Although not shown in FIG. 1, system 100 may include other sensors in proximity to debris removal opening 110 to detect when footwear is in proximity and/or in contact with debris remover 134. Another sensor may monitor the amount of debris collected in debris removal drawer 138. Drawer 138 may store debris removed from footwear and provide for convenient removal and disposal of the debris. Proximity sensors may be positioned at the user entry portal 140 and/or user exit portal 142 to detect when a user enters or exits the pathway of the system respectively. Sensors may include, without limitation, optical sensors, pressure sensors, sonic sensors, haptic sensors, and temperature sensors.

Housing 102 may include a user interface arranged to provide one or more cues to a user during operations of the device. The user interface may include display 120, one or more visual indicator elements on top surface 104, and one or more audio speakers that may issue audio commands and/or beeps to a user to perform certain actions during the cleaning and sanitization process. The cues may include an instruction to a user to position their footwear sole or soles over the debris removal opening 110, position their footwear sole or soles over the sanitizing interfaces 112, enter and/or step onto portions of top surface 104 such as, for example, stepping areas 130 when the user enters user entry portal 140, and/or exits or step off top surface 104 via user exit portal 142. System 100 may include a phone caddie 122 and/or storage container which may be arranged to hold a user's phone and/or may be configured to clean and sanitize the user's phone.

Figure 4:
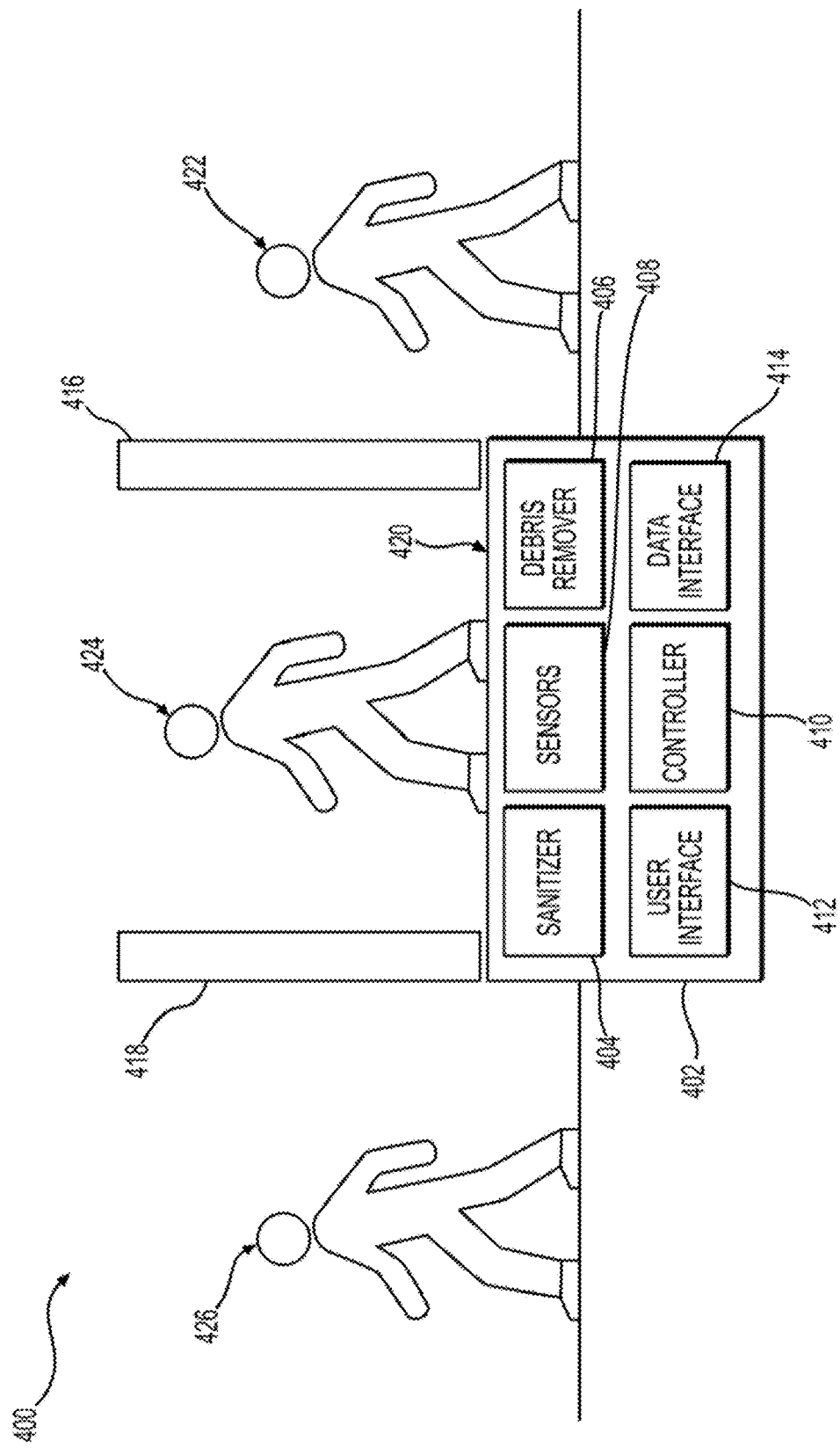
FIG. 4 is a block diagram of a sole debris cleaning and sanitization system and/or device that illustrates a user's position before, during, and after the debris cleaning and sanitization process.

System 100 may include a controller, e.g., controller 410 of FIG. 4, arranged to: i) receive sensor data from the one or more sensors such as sensors 128; i) control operations of the debris remover 134 and/or sanitizer in 148 response to the received sensor data, and iii) send cue instructions associated with the one or more cues to the user interface for display to a user via, for example, display 120. The controller may include a computer system.

Figure 2:
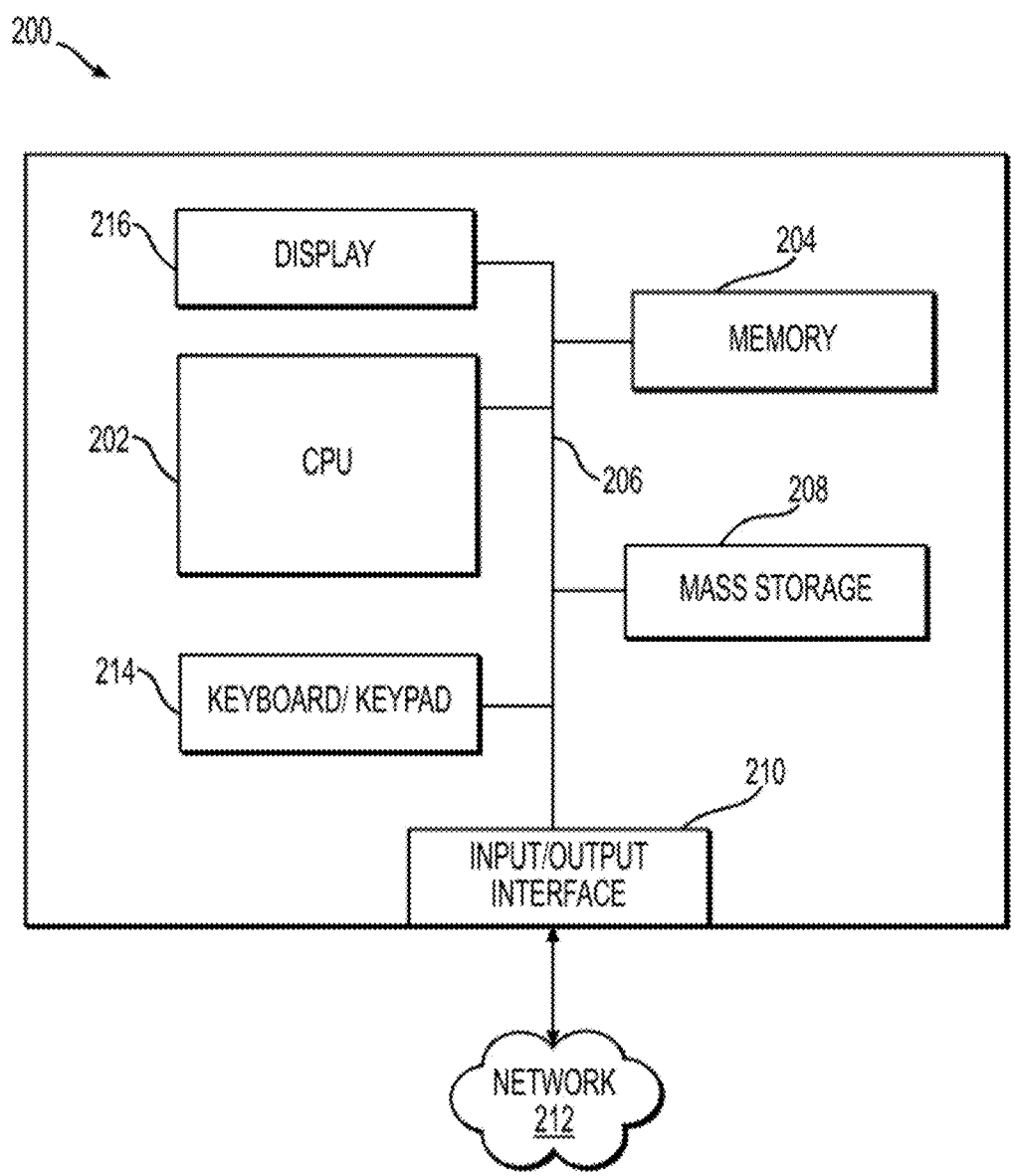
FIG. 2 shows a diagram of a computer system.

FIG. 2 includes a block diagram of a computer system 200 for performing the functions of a computer such as for the controller associated with FIG. 1 and/or controller 410 of FIG. 4. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives or solid state memory, for storing data and instructions for use by the CPU 202. At least one component of the mass storage system 208, preferably in the form of a disk drive, solid state, or tape drive, stores the database used for processing sensor data and/or controlling operations of system 100 and/or 400. The mass storage system 208 may also include one or more drives for various portable media, such as a floppy disk, flash drive, a compact disc read only memory (CD-ROM, DVD, CD-RW, and variants), memory stick, or an integrated circuit non-volatile memory adapter (i.e. PC-MCIA adapter) to input and output data and code to and from the computer system 200.

The computer system 200 may also include one or more input/output interfaces for communications, shown by way of example, as interface 210 and/or transceiver for data communications via the network 212 (or network 104 of FIG. 1). The data interface 210 may be a modem, an Ethernet card or any other suitable data communications device. To provide the functions of a computer 102, the data interface 210 may provide a relatively high-speed link to a network 212, such as an intranet, or the Internet, either directly or through another external interface. The communication link to the network 212 may be, for example, optical, wired, or wireless (e.g., via satellite or cellular network). Alternatively, the computer system 200 may include a mainframe or other type of host computer system capable of Web-based communications via the network 212. The computer system 200 may include software for operating a network application such as a web server and/or web client.

The computer system 200 may also include suitable input/output ports, that may interface with a portable data storage device, or use the interconnect bus 206 for interconnection with a local display 216 and keyboard 214 or the like serving as a local user interface for programming and/or data retrieval purposes. The display 216 and/or display 120 may include a touch screen capability to enable users to interface with the system 200 by touching portions of the surface of the display 216. Remote operations personnel may interact with the system 200 for controlling and/or programming the system from remote terminal devices via the network 212.

The computer system 200 may run a variety of application programs and store associated data in a database of mass storage system 208. One or more such applications may include a cleaning and sanitization process that controls various components of system 100 and/or provides cue to a user to perform certain actions during the cleaning and sanitization process.

The components contained in the computer system 200 may enable the computer system to be used as a server, workstation, personal computer, network terminal, mobile computing device, and the like. As discussed above, the computer system 200 may include one or more applications that enable cleaning and sanitization of a footwear sole or soles. The system 200 may include software and/or hardware that implements a web server application. The web server application may include software such as HTML, XML, WML, SGML, PHP (Hypertext Preprocessor), CGI, and like languages.

The foregoing features of the disclosure may be realized as a software component operating in the system 200 where the system 200 includes UNIX workstation, a Windows workstation, a LINUX workstation, or other type of workstation. Other operating systems may be employed such as, without limitation, Windows, MAC OS, and LINUX. In some aspects, the software can optionally be implemented as a C language computer program, or a computer program written in any high level language including, without limitation, JavaScript, Java, CSS, Python, PHP, Ruby, C++, C, Shell, C#, Objective-C, Go, R, TeX, VimL, Perl, Scala, CoffeeScript, Emacs Lisp, Swift, Fortran, or Visual BASIC. Certain script-based programs may be employed such as XML, WML, PHP, and so on. The system 200 may use a digital signal processor (DSP).

As stated previously, the mass storage 208 may include a database. The database may be any suitable database system, including the commercially available Microsoft Access database, and can be a local or distributed database system. A database system may implement Sybase and/or an SQL Server. The database may be supported by any suitable persistent data memory, such as a hard disk drive, RAID system, tape drive system, floppy diskette, or any other suitable system. The system 200 may include a database that is integrated with the system 200, however, it is understood that, in other implementations, the database and mass storage 208 can be an external element.

In certain implementations, the system 200 may include an Internet browser program and/or to be configured to operate as a web server. In some configurations, the client and/or web server may be configured to recognize and interpret various network protocols that may be used by a client or server program. Commonly used protocols include Hypertext Transfer Protocol (HTTP), File Transfer Protocol (FTP), Telnet, and Secure Sockets Layer (SSL), and Transport Layer Security (TLS), for example. However, new protocols and revisions of existing protocols may be frequently introduced. Thus, in order to support a new or revised protocol, a new revision of the server and/or client application may be continuously developed and released.

The computer system 200 may include a web server running a Web 2.0 application or the like. Web applications running on system 200 may use server-side dynamic content generation mechanisms such, without limitation, Java servlets, CGI, PHP, or ASP. In certain embodiments, mashed content may be generated by a web browser running, for example, client-side scripting including, without limitation, JavaScript and/or applets on a wireless device.

In certain implementations, system 100, 200, and/or 400 may include applications that employ asynchronous JavaScript+XML (Ajax) and like technologies that use asynchronous loading and content presentation techniques. These techniques may include, without limitation, XHTML and CSS for style presentation, document object model (DOM) API exposed by a web browser, asynchronous data exchange of XML data, and web browser side scripting, e.g., JavaScript. Certain web-based applications and services may utilize web protocols including, without limitation, the services-orientated access protocol (SOAP) and representational state transfer (REST). REST may utilize HTTP with XML.

The systems 100, 200, and/or 400 may also provide enhanced security and data encryption. Enhanced security may include access control, biometric authentication, cryptographic authentication, message integrity checking, encryption, digital rights management services, and/or other like security services. The security may include protocols such as IPSEC and IKE. The encryption may include, without limitation, DES, 3DES, AES, RSA, and any like public key or private key based schemes.

Generally, the inventive debris cleaning and sanitization process may include a sequence of stages where certain operations and/or user actions are performed. First, debris removal brushes of debris remover 134 and/or 406 engage and/or are activated by controller 410 upon a detected presence of a user's footwear within the vicinity of debris removal opening 110. Narrow heeled shoes may be accommodated via placement of a high heel in designated stop area 136. A brush motor that was driving and/or rotating the brushes of debris remover 134 disengages when the footwear is detected by a sensor as being removed from the brushes and/or the debris removal opening 110. In one implementation, the duration in which the one or more brush motors are engaged is by default, infinite while a sensor detects that footwear is in the vicinity of the debris removal opening 110. This duration may be established during the system commissioning.

Figure 3C:
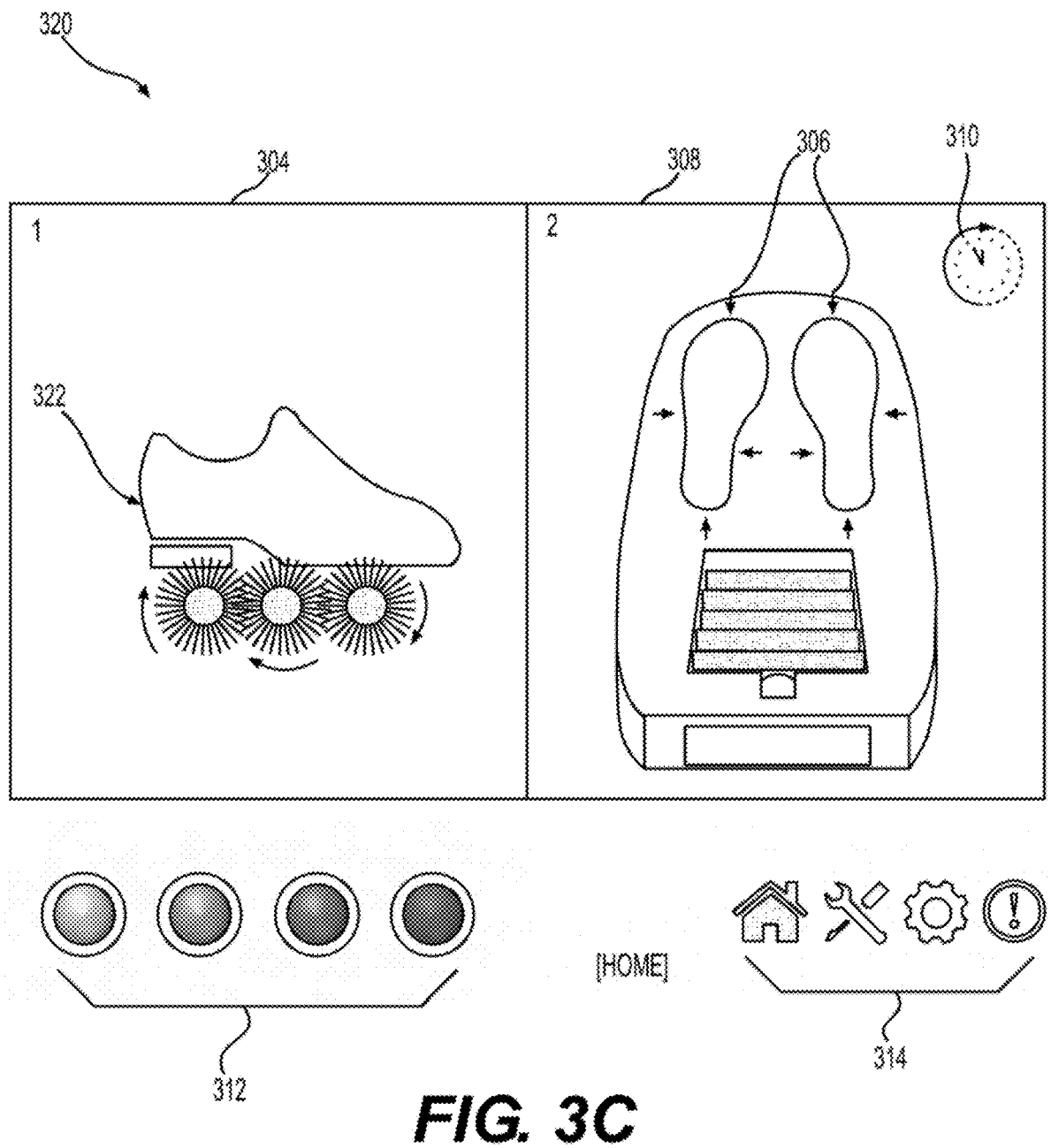

As debris accumulates in debris removal drawer 138, it may be discarded when full, which may be monitored for available capacity by a controller such as controller 410 via a drawer sensor. In some implementations, system 100 and/or 400 prompts, via a user interface such as interface 412 and/or display 120 for debris removal periodically, such as once daily. Custom drawer liners may line drawer 138 to simplify the debris removal process. After debris removal, a user places their shoes on sanitization areas defined by sanitization interfaces 112. An LED indication may provide proper placement feedback to a user of the shoe position(s). One or more LED indicators may be placed adjacent to the sanitization areas and/or display 120 may provide a graphical image of LED indicators such as shown in FIG. 3A-3C of indicators surrounding the sanitization areas. A red indicator may indicate that footwear placement is not properly aligned with sanitization interfaces 112 while a green indicator may indicate proper alignment of footwear. Audio, visual, and/or haptic commands and/or feedback may be provided alternatively or additionally to the user to effect proper footwear alignment via, for example, interface 412. Footwear placement indicators may be activated and deactivation by controller 410 based on sensor data received from sensors such as sensors 128 that indicator the presence or absence of footwear in certain locations on the top surface 104.

Once proper alignment is achieved, UV sanitization of footwear soles is activated by, for example, controller 410. The duration of sanitization may be configured by default by the manufacturer, by a controller such as controller 410, remotely by a remote programmer, and/or manually by a user. In one implementation, the sanitization duration, e.g., the duration that. UV emitters are activated and emit UV light, may be about 8-10 seconds. The range of UV emitter activation duration may be adjustable from 1 second up to 180 seconds, or longer. In one implementation, an LED indication of the sanitization process is provided while sanitization occurs. A UV ray shield such as UV shield 124 may protect the user from direct. UV light rays that escape past the user's footwear during sanitization. The UV shield 124 may be foldable toward and away from the user and/or pathway. Controller 410 may engage a motor to deploy UV shield 124 before UV emitter activation and retract UV shield 124 after UV emitter activation. UV shield 124 may also function as a gate to inhibit a user from exiting via the user exit portal 142 until the sanitization function is completed.

When sanitization is complete, UV light(s) and emitters turn off and/or are instructed to turn off by controller 410 and the sanitization LED indication ceases. A user may be visually and/or audibly prompted to exit the machine top surface 104 at the opposite end from which he/she entered, i.e., via the user exit portal 142. A display such as display 120 and/or speaker may provide visual and/or audio confirmation and feedback to a user, as well as provide function, stage, and/or error status information to the user. Audio feedback may include simulated voice phrases and/or one or more audio beeps.

Figure 3G:

FIGS. 3A-3G show a series of user interface screen shots 300, 316, 320, 340, 350, 360, and 380 displayed to a user as they operate the exemplary sole debris cleaning and sanitization systems 100 and/or 400 during various stages of the cleaning and sanitization process. FIG. 3A includes a screen shot 300 of display 120 indicating that system 100 and/or 400, i.e., the unit, is ready for cleaning and sanitization of a user's footwear sole(s). FIG. 3B includes a screen shot 316 of display 120 including a shoe size menu or table 318. Display 120 may via, for example, a touchscreen, enable a user to input their footwear size to the system 100 and/or 400. System 100 and/or 400 may use the inputted footwear size to configure sanitizer 404 to emit UV light over an area toward the footwear sole over an area corresponding to the sole size. FIG. 3C includes a screen shot 320 of display 120 indicating when the system 100 and/or 400 is operating in the sole debris removal stage. FIG. 3D includes a screen shot 340 of display 120 indicating when the system 100 and/or 400 is operating in the sanitization stage. FIG. 3E includes a screen shot 350 indicating that system 100 and/or 400 has completed the sanitization stage by, for example, removing an illumination within a footwear outline 352 and/or illuminating a yellow color icon of indicator 312. FIG. 3F includes a screen shot 360 of display 120 showing a troubleshooting information page or table 362 regarding status of systems 100, 200, and/or 400. FIG. 3G includes a screen shot 380 of display 120 showing programmable settings associated with various components of systems 100, 200, and/or 400 in table 382.

Screen shot 300 of FIG. 3A may include a footwear position image 302 in a first section 304 and a sanitization status based on indicators 306 in section 308. Footwear position image 302 shows that no footwear is engaged with debris remover 134 and/or 406. Section 308 may include a timer indicator 310 that indicates to a user the duration and/or remaining amount of time that UV emitters will be activated. Indicator 310 may include an analog clock image, counter, and/or status bar that indicates a remaining amount of time that sanitization will be activated. Screen shot 300 may include one or more status indicators 312 that indicate status of the system and/or whether system 100 and/or 400 is ready to perform a stage of the cleaning and sanitization.

For example, different colored indicators may be used to indicate different stages and/or different statuses of systems 100 and/or 400. For example, a green indicator 312 may be illuminated when the system 100 and/or 400 is ready to operate and/or a particular stage is ready to be initiated or is in operation. Status indicators may be illuminated according to table 362 of FIG. 3D. Screen shot 300 may include one or more selectable icons 314 that enable a user to navigate to various screens or return to a "Home" screen, navigate to a troubleshooting page, navigate to a system configuration page, and/or navigate to an information and/or search page. Screen shots 320 and 340 may have the same or similar visual indicators and/or images as screen shot 300. Screen shots 320, 340, 360 and 380 may also include navigation and/or system icons 314. Screen shot 380 may also include a settings table 382 that enables a user to configure certain setting such as, for example, UV emitter activation duration.

In one implementation, system 100 and/or 400 may operate to perform footwear sole(s) cleaning and sanitization according to the follow operations. Display 120 and/or user interface 412 may illuminate a "Ready" LED and/or indicator such as green indicator 312, indicating that system 100 and/or 400 is ready for use. A user may then place one foot onto sole debris remover 134 and/or debris removal surface (brush area) at debris removal opening 110. One or more sensors may sense the presence of the users footwear. In response to detecting the footwear, display 120 may have a debris removal stage indicator and/or LED start blinking. After about a 1 second delay, controller 410 may initiate the debris removal process by engaging and/or activating one or more brush motors. Display 120 and/or interface 412 may change the illumination of the debris removal stage indicator and/or LED from blinking to solid illumination on display 120. Display 120 via screen shot 320 may show position image 322 indicating that the footwear is engaged and/or in the vicinity of debris remover 134.

The debris removal process continues until one or more sensors sense that the foot and/or footwear is no longer present and/or within the vicinity of debris remover 134 or the process has timed out. Once the debris remover timer has timed out or the absence of footwear is detected and sensor data of such status is received by controller 410, controller 410 may deactivate the brush cleaning motors to stop the debris cleaning brushes from rotating. Also, the debris removal indicator and/or LED may be turned off and the "Ready" indicator and/or LED is illuminated. System 100 and/or 400 may include an E-Stop (emergency stop) button that a user may select on a support handle and/or rail 118 to deactivate the brush cleaning motors.

A user may then place one foot onto one or more of the UV sanitizer interfaces 112 and/or sanitization areas. Sensors such as sensor 128 may detect the presence of the user's shoe and send sensor data to controller 410 while display 120 may illuminate a sanitization stage indicator and/or LED that blinks on display 120. Green/Red Arrows may indicate correct/incorrect shoe sole positioning with respect to the one or more sanitizing interfaces 112 on display 120 and/or via indicator elements on top surface 104. When a shoe is properly positioned, the green position arrows change from red to green and hold.

The user may then place their second foot onto the remaining sanitization area of the sanitizing interfaces 112. Sensors 128 may then detect the presence of the second shoe and send sensor data to controller 410 to indicate the presence of the second shoe in the vicinity of sanitizing interfaces 112. Green/Red Arrows may indicate correct/incorrect shoe sole positioning via display 120 and/or via indicator elements on top surface 104. When the second shoe is properly positioned, the green position arrows illuminate and hold. After both shoes are properly positioned, sanitization stage indicator and/or LED of display 120 blinks rapidly for about 2 seconds. After two seconds, the sanitization stage indicator and/or LED illuminates solid and a sanitization graphic is engaged on display 120. UV sanitization emitters may be activated and/or engaged for the prescribed and/or configured duration. When the UV sanitizing process is complete, the UV Emitters are shut off by controller 410, sanitization indicators and/or LED indication ends, the sanitization graphic turns off, and the Ready indicator and/or LED is illuminated.

Whenever controller 410 in response to, for example, sensor data, detects a fault, display 120 and/or interface 412 may illuminate a red indicator and/or LED and/or warning icon to indicate to a user that a fault has occurred. This may include a motor failure, overheating, UV emitter failure, and the like. System 100 and/or 400 may include optional cell phone sanitization and charging functions that may operate independently from sole cleaning and sanitizing functions. Display 120 and/or interface 412 may include representative icons that will be displayed accordingly during the respective phone functions. In certain configurations, both UV sanitization and debris cleaning are not operated simultaneously. In one implementation, no functions can be performed while system 100 and/or 400 is in a fault mode and/or stage. System 100 and/or 400 may prompt a user to discard collected debris from debris collection drawer 138 periodically such as once daily.

FIG. 4 is a block diagram of a footwear sole debris cleaning and sanitization system and/or device 400 that illustrates a user's position before 422, during 424, and after 426, the debris cleaning and sanitization process. System 400 includes a housing 402 having a footwear sanitizer 404, debris remover 406, sensors 408, a controller 410, a user interface 412, and data interface 414. Housing 402 may include a top surface 420 and/or 104 on which a user may stand in, for example, position 424. System 400 may also include user entry portal 416 and user exit portal 418.

User entry portal 416 may include a gate or other movable barrier that allows a user to step onto top surface 420, but prevents the user from stepping back off the top surface to position 422 to prevent possible re-contamination of the user's footwear. The barrier may include, without limitation, a swing arm, a railing, a single swinging panel, dual swinging panel, and a turn-style. The barrier may be configured to swing inwardly toward user exist portal 418 from a substantially perpendicular orientation with respect to a railing such as railing 116, to a substantially parallel orientation with respect to railing 116 to allow a user to enter the pathway on top surface 420. The barrier, however, may not be configured to swing backwards toward position 422 to prevent a user from back tracking from top surface 420 through the user entry port 416. The barrier may be mounted on and/or extend from railing 114 and/or 116. The barrier may be mounted independently on housing 402. User exit portal 418 may include a similar barrier as described with respect to user entry portal 416 to possibly prevent a user from stepping on top surface 420 from user exit portal 418 and/or to prevent a user from prematurely exiting the top surface 420 before the sanitization process is completed. As previously discussed, UV shield 124 may also function as a barrier to prevent an improper entry or a premature exit by a user.

Figure 5:
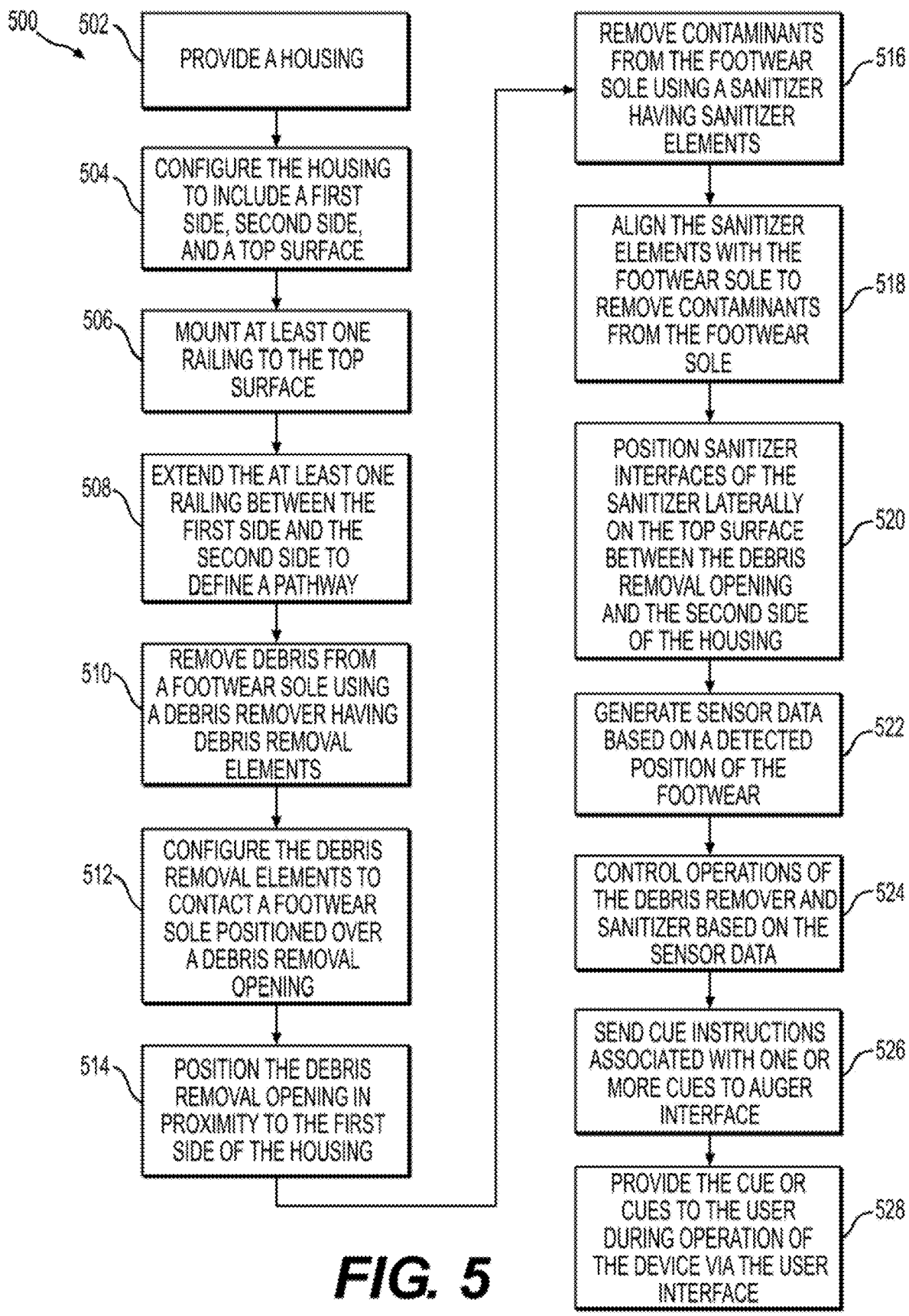
FIG. 5 shows a process for performing debris cleaning and sanitization.

FIG. 5 shows a process 500 for performing debris cleaning and sanitization. Process 500 includes: providing a housing 102 and/or 402 (Step 502) and configuring the housing 102 and/or 402 to have: a top surface 104 and/or 420 arranged to support a user while standing on the top surface 104 and/or 420, a first side 106 positioned adjacent to a user entry portal 140 and/or 416, and a second side 108 positioned on an opposing side of the housing 102 to the first side 106 where the second side 106 is positioned adjacent to a user exit portal 142 and/or 418 (Step 504); mounting at least one railing 114 and/or 116 on the top surface 104 and/or 420 (Step 506); extending the at least one railing 114 and/or 116 between the first side 106 and the second side 108 of the housing 102 and/or 402, where the at least one railing 114 and/or 116 defines a pathway through which the user passes along from the user entry portal 140 and/or 416 to the user exit portal 142 and/or 418 (Step 508); removing debris from the footwear sole using a debris remover 134 and 406 having one or more debris removal elements extending toward a debris removal opening 110 in the top surface 104 and/or 420 (Step 510); configuring the one or more debris removal elements to contact the footwear sole while the footwear sole is positioned over the debris removal opening 110 (Step 512); and positioning the debris removal opening 110 in proximity to the first side 106 of the housing 102 and/or 402 (Step 514).

Process 500 further includes: removing contaminants from the footwear sole using a sanitizer 148 and/or 404 having one or more sanitizing elements directed toward one or more sanitizing interfaces 112 in the top surface 104 and/or 420 (Step 516); aligning the one or more sanitizing elements with the footwear sole while the footwear sole is positioned over the one or more sanitizing interfaces 112 and removing contaminants from the footwear sole (Step 518); positioning the one or more sanitizing interfaces 112 laterally on the top surface 104 and/or 420 between the debris removal opening 110 and the second side 108 of housing 102 and/or 402 (Step 520); generating sensor data from one or more sensors such as sensors 128 based on at least one of a detected position of the footwear sole, detected a position of the user, detected temperature of the device, detected presence of debris on the footwear sole, and detected presence of a contaminant on the footwear sole (Step 522); controlling operations of at least one of the debris remover 134 and/or 406 and sanitizer 148 and/or 404 in response to the sensor data (Step 524); sending cue instructions associated with the one or more cues to a user interface 412 including display 120 (Step 526); and providing the one or more cues to the user during operations of the system via the user interface 412, where the one or more cues includes an instruction to the user to position the footwear sole over at least one of the debris removal opening 110 and the sanitizing interfaces 148.

FIGS. 6A, 6B, and 6C show a specification table 600 for an exemplary configuration of a debris cleaning and sanitization system such as system 100 and/or 400.

Figure 7:
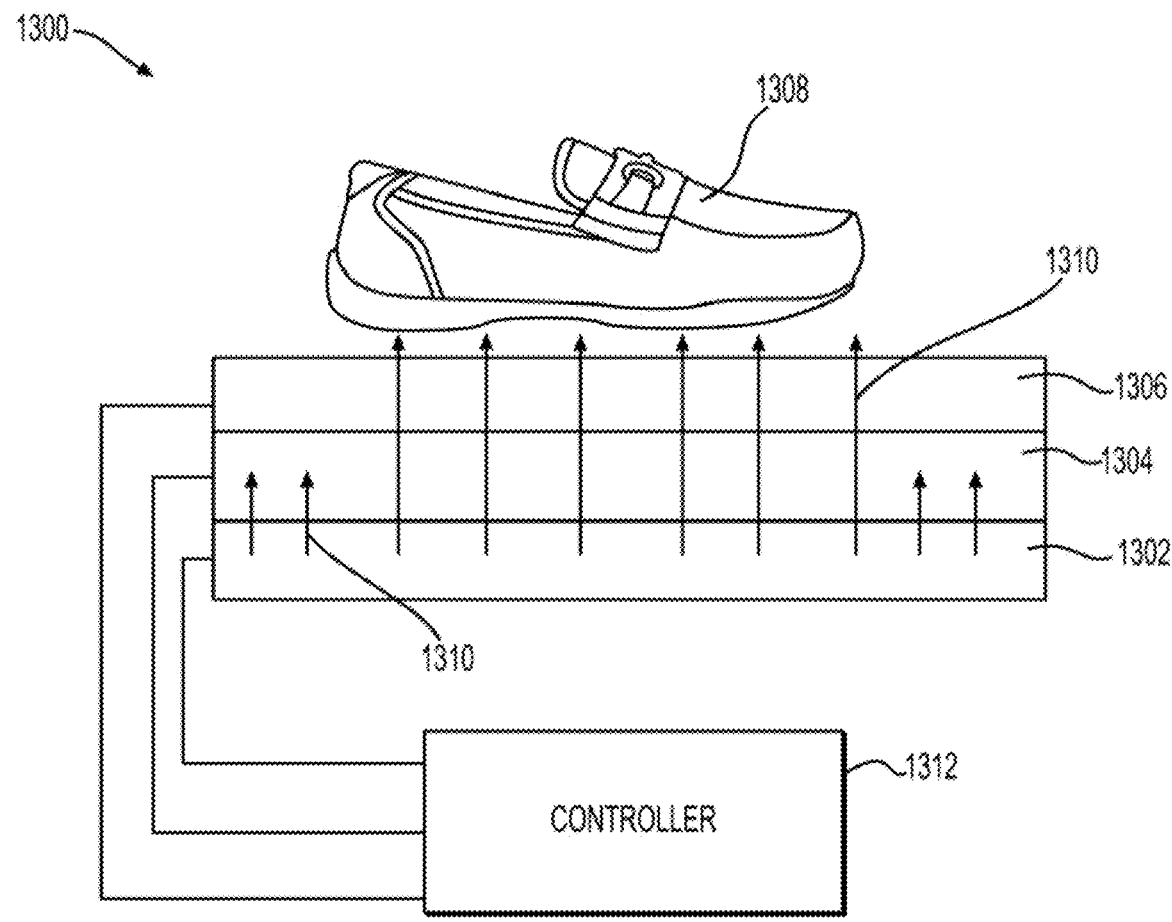
FIG. 7 is a cross-sectional view of a UV sanitization system including a UV shielding layer.

FIG. 7 is a cross-sectional view of a UV sanitization system 1300 such as may be implemented in sanitizer 404 or system 100 including a UV light source layer 1302, UV light blocking layer 1304, and a footwear sensing layer 1306 that may be in contact with a user's footwear 1308. Footwear sensing layer 1306 may be arranged to detect the presence and/or size of footwear 1308 positioned above layer 1306. Footwear sensing layer 1306 may include a touchscreen and/or touch-sensitive surface arranged to sense the footwear 1306 size and/or position. Layer 1306 may include a resistive touchscreen, capacitive touchscreen, a projected capacitive touchscreen, an infrared touchscreen, and/or a surface acoustic wave (SAW) touch screen. Light blocking layer 1304 may include switchable glass to control the transmission of UV light from a UV light source in layer 1302 toward footwear 1308. UV light blocking layer 1304 may include a planar array of microshutters arranged to selectively allow UV light to pass through toward footwear 1308 while selectively blocking UV light that would otherwise escape past footwear 1308 and possibly toward a user's body. Switchable glass of layer 1304 may include passive or active elements. For example, microshutters are active elements that close or open to block or allow light to pass through respectively. Layer 1304 may include electrochromic switchable glass. Microshutters may include microblinds. Microshutters may be based on curling electrodes and/or microelectromechanical systems (MEMS). System 1300 may include an additional translucent and/or transparent layer positioned above layer 1306 and arranged to act as a sanitizing interface.

In operation, light source layer 1302 may include one or more UV light emitters arranged to emit UV-A, UV-B, and/or UV-C light 1310 toward footwear 1308. Layer 1306 senses the presence and/or size of footwear 1308. Layer 1306 may sense the area of the sole of footwear 1308 in contact with or close proximity to a top surface of layer 1306. Layer 1306 may provide sensor data to controller 1312 and/or controller 410. Based on the sensor data received, controller 1312 or 410 may send instructions to layer 1304 and/or various elements thereof (e.g., shutters) to selectively activate (e.g., open) shutters to allow UV light to pass through and toward the sole of footwear 1308 while selectively de-activating (e.g., close) shutters to block UV light in areas of the top surface of layer 1306 that are not in contact with or in close proximity to the sole of footwear 1308. Controller 1312 and/or 410 may also control activation of the one or more UV light emitters of UV light source layer 1302 based on the detected presence of footwear 1308.

Figure 8:
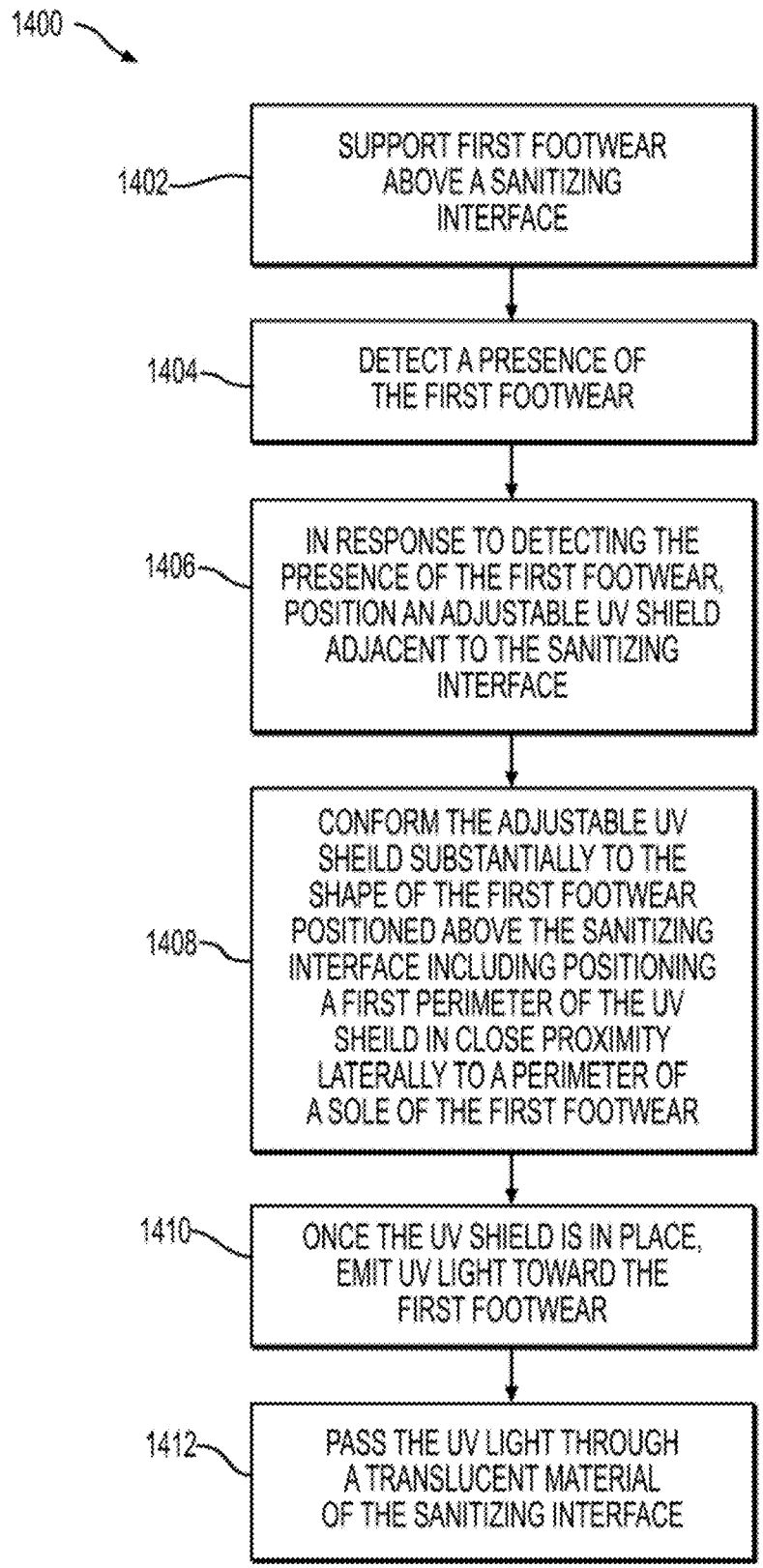
FIG. 8 shows a process for providing UV shielding.

FIG. 8 shows a process 1400 for providing UV shielding including: supporting first footwear, such as footwear 1102, positioned above a sanitizing interface such as interface 112 (Step 1402); detecting a presence of the first footwear 1102 using one or more sensors 408 (Step 1404); in response to detecting the presence of the first footwear, positioning an adjustable UV shield such as UV shield 1200 adjacent to the sanitizing interface 112 (Step 1410); and conforming the adjustable UV shield 1200 substantially to a shape of the first footwear 1102 positioned above the sanitizing interface 112 including positioning a first perimeter of the adjustable UV shield 1200 in close proximity laterally to a perimeter of a sole of the first footwear 1102 (Step 1412), emitting UV light from an UV emitter such as emitter 1212 toward the first footwear 1102 (Step 1406); passing the UV light through a translucent material of the sanitizing interface 112 (Step 1408).

Figure 9A:
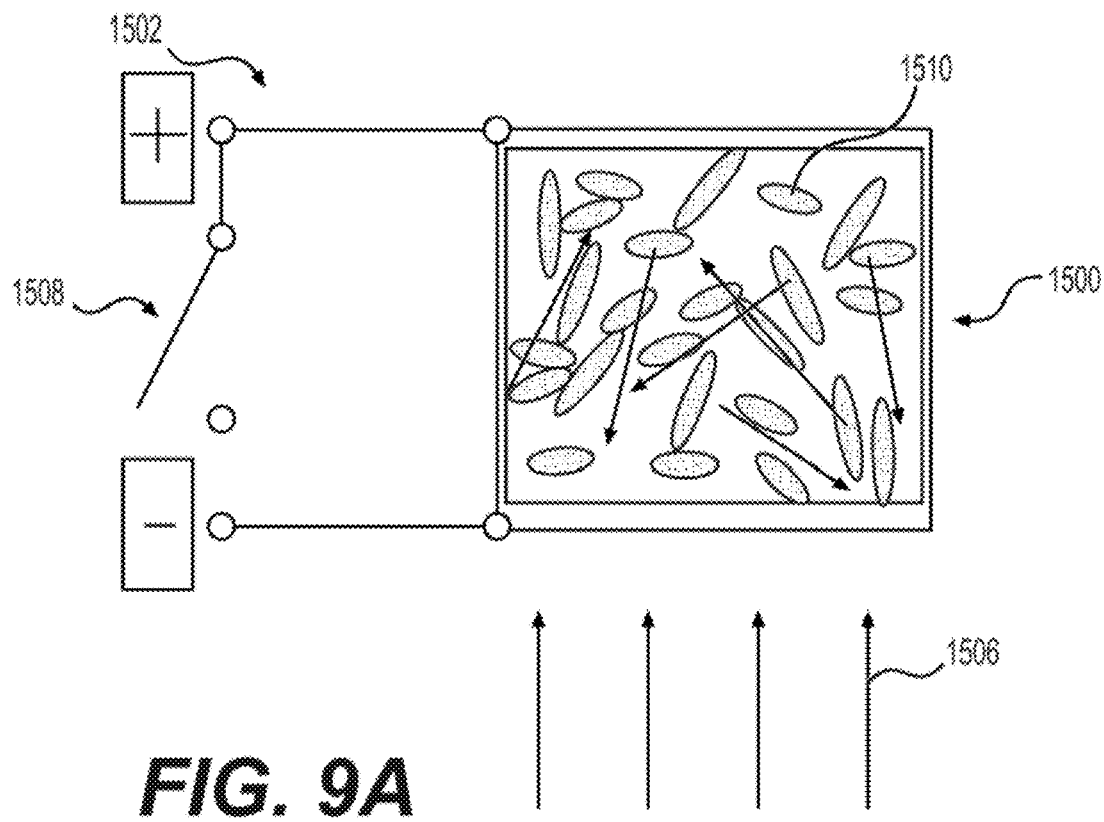
FIGS. 9A and 9B illustrate a shutter in the open or pass through position and in a closed or blocking position.
Figure 9B:
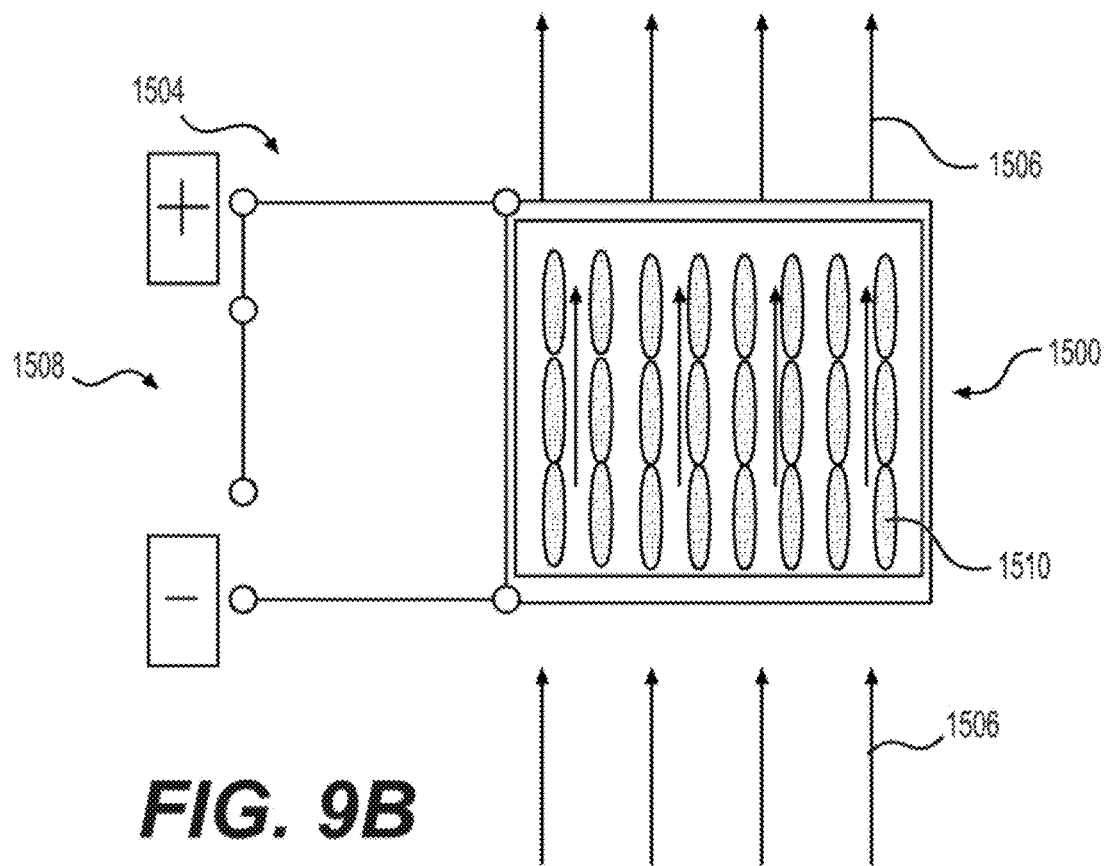

FIGS. 9A and 9B illustrate a cell and/or shutter 1500 in a closed or blocking position 1502 and in an open or pass through position 1504 respectively. When switch 1508 is open, there is no voltage potential difference across the cell 1500 and, therefore, the elements 1510 are not aligned, which blocks the UV light 1506 from passing through the cell 1500. When switch 1508 is closed, there is a voltage potential across the cell 1500 which causes the elements 1510 to be aligned in parallel to, thereby, allow the UV light 1506 to pass through the cell 1500. In some implementations, each shutter and/or cell 1500 includes a miniaturized polymer-dispersed liquid crystal (PDLC) and/or PDLC-like device that becomes transparent when an electric current is supplied to it. Each shutter and/or cell 1500 may contain a layer with droplets of polarized, light-blocking microscopic elements and/or liquid crystals (LC) 1510. In the natural (non-energized/no voltage applied/no current) state, these LC elements 1510 are randomly arranged within each cell 1500 and do not permit passage of UV-C light. However, when energized with an appropriate, low DC voltage, the LC components and/or elements 1510 align themselves in the cell and create open slits through which the UV-C light passes.

Figure 10A:
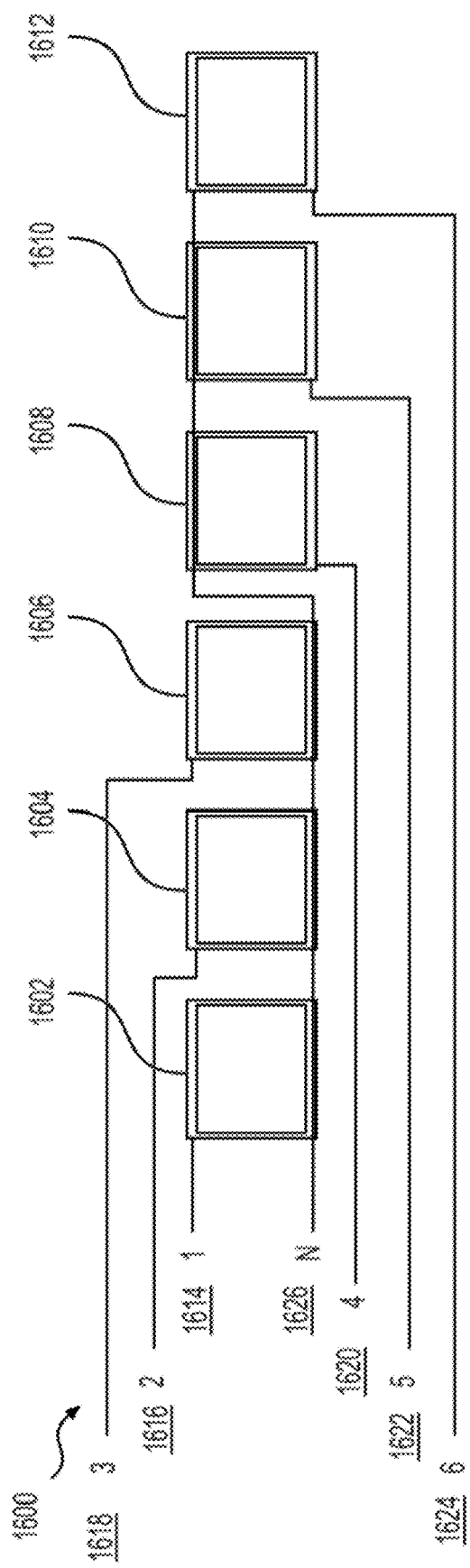
FIG. 10A shows a row of shutters including power control signal inputs.

FIG. 10A shows a row 1600 of cells 1602 through 1612 including power control signal input lines 1614 through 1624. In this configuration, all of the cells 1602 through 1612 share a common return or negative input line 1626. A voltage and/or current applied via control signal input lines 1614 through 1624 may be controlled by a microprocessor and/or controller 1312. Controller 1312 may, for example independently control each cell 1602 through 1612 by switching voltages and/or current on each control signal input line 1614 through 1624. For example, to place cell 1602 in an open and/or pass through state, controller 1312 applies a voltage and/or current to cell 1602 via input line 1614 that creates a current through cell 1602 between input line 1614 and return line 1626 to align its LC elements to allow light to pass through the cell 1602. Controller 1312 can selectively set any of cells 1602 through 1612 to a closed state by removing a voltage and/or current applied to a selected cell via its respective input line 1614 through 1624. While the cells 1602 through 1612 include LC elements, other types of cells and/or shutters may be used including, for example, microelectromechanical (MEMS) based shutters.

Figure 10B:
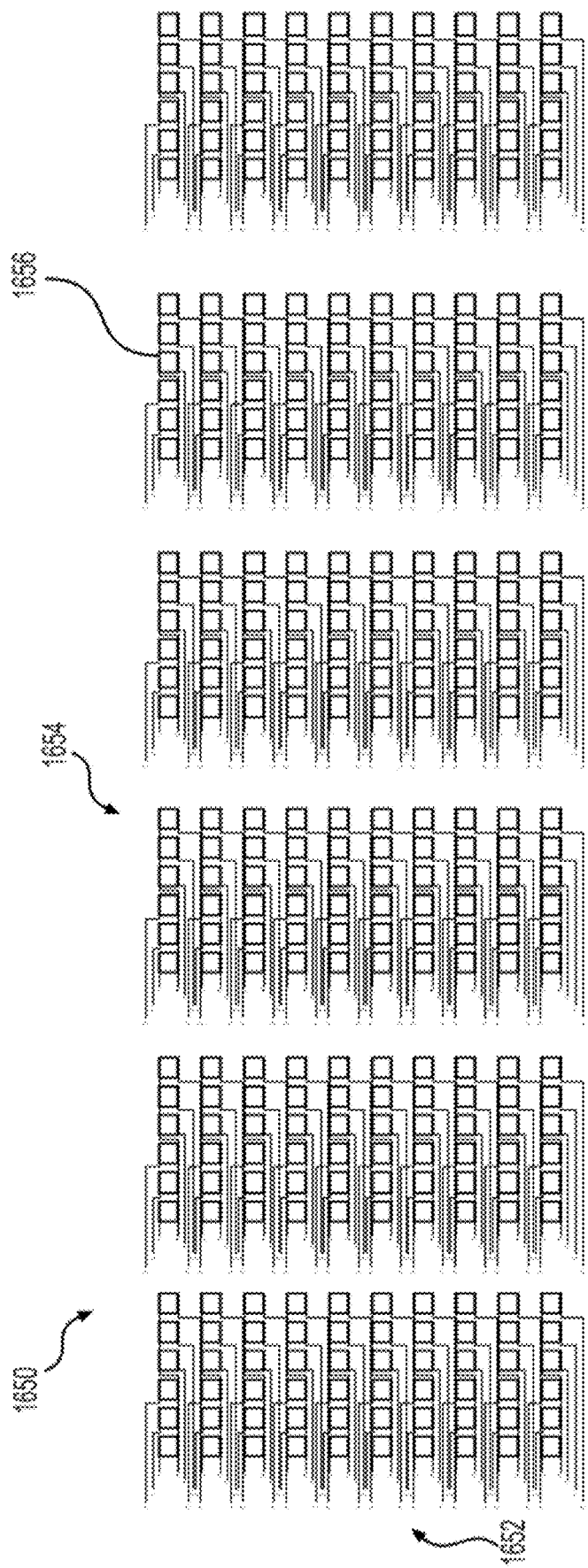
FIG. 10B shows an array of shutters arranged in multiple rows and columns.

FIG. 10B shows an array 1650 of cells and/or shutters arranged in multiple rows 1652 and columns 1654. In some implementations, array 1650 includes a tightly arranged array of miniature cells 1656 that can be individually actuated by a processor such as controller 1312 to be either opened or closed based on their X-Y coordinate location in the array 1650. Controller 1312 may access a table and/or database in a memory such as memory 204 that maps each cell of the array 1650. Each entry of the table may store a 1 for an open or activated cell and a 0 for a closed or deactivated cell. Each entry may be set based on shape data received from at least one shape sensor that detects the shape of a surface of footwear facing a sanitizing interface. Controller 1312 may review the table to determine which cells of array 1656 to open or close for screening cells or to activate or deactivate for light emitter cells. For example, cell 1656 is the fifth cell in row 1 of array 1650. Hence, its X-Y coordinates in the table may be (5,1).

Figure 11A:
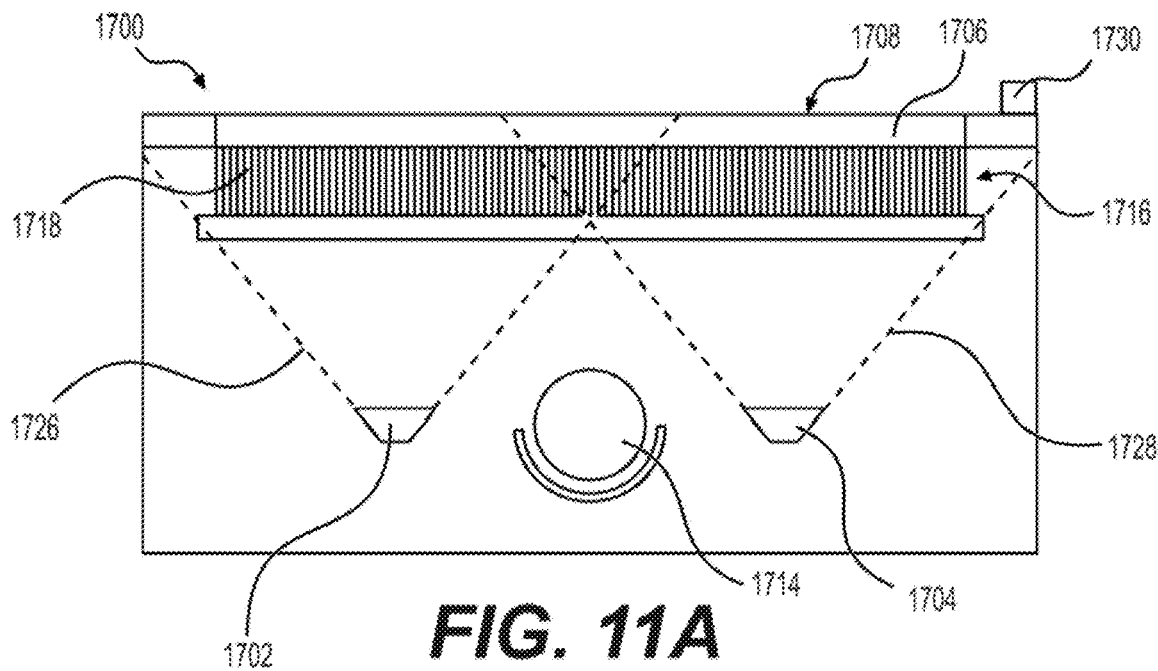
FIG. 11A shows a UV sanitizing housing including optical sensors arranged to detect the presence of an object such as footwear.
Figure 11B:
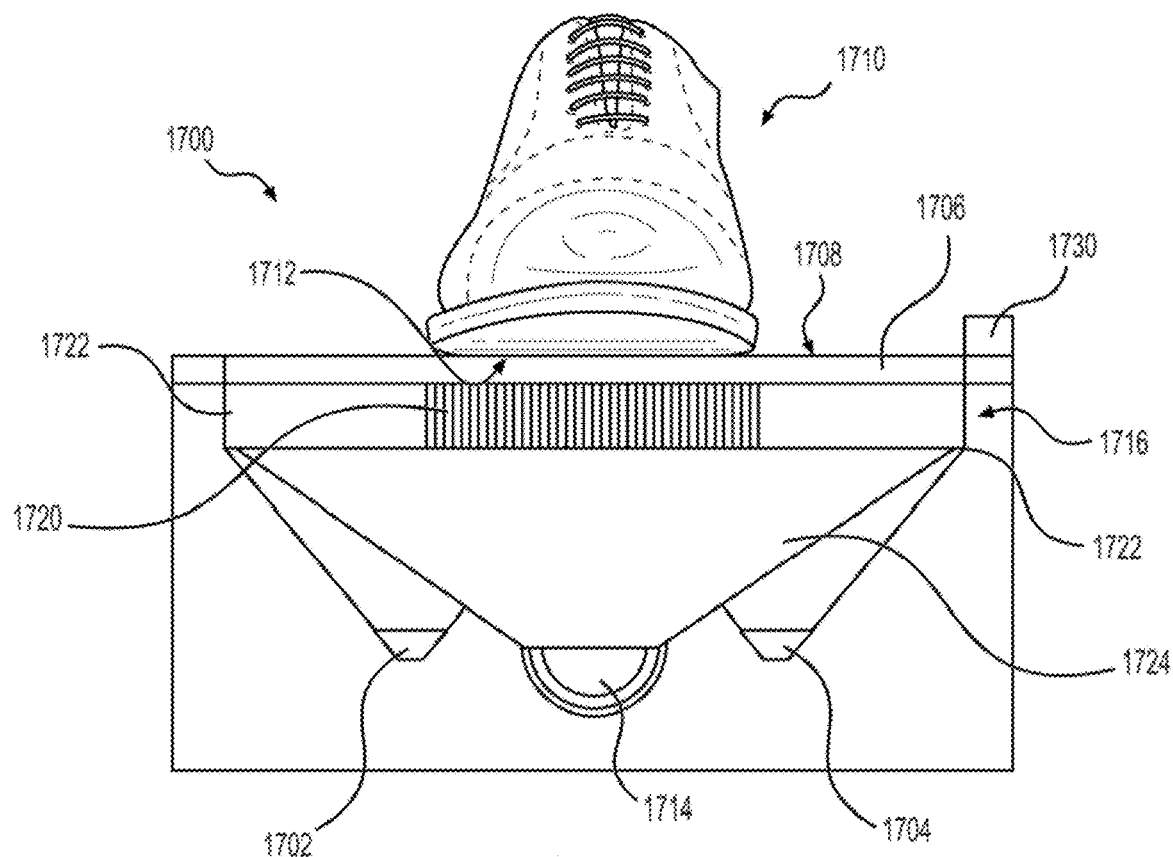
FIG. 11B shows the UV sanitizing housing of FIG. 17A when the UV emitter is emitting light while a portion of the shutters are open to pass through UV light toward the footwear and another portion of the shutters are closed to block UV light not directed toward the footwear.

FIG. 11A shows a UV sanitizing housing 1700 during a footwear detection phase including optical shape sensors 1702 and 1704 arranged to detect the presence of an object such as footwear 1710. FIG. 11B shows the UV sanitizing housing 1700 when the UV emitter 1714 is emitting UV light 1724 while a portion 1720 of the shutters and/or cells 1718 are open to pass through the UV light 1724 toward footwear 1710 while another portion 1722 of the shutters and/or cells 1718 are closed to block UV light 1724 not directed toward the footwear 1710. The shape sensors 1702 and 1704 are able to detect the 2-dimensional extent of the shape of the object that is in close proximity to the top surface of housing 1700 using optical detection signals 1726 and 1728 respectively. Housing 1700 includes a sanitizing interface 1706 including a top surface 1708 arranged to support footwear 1710 positioned above the sanitizing interface 1706. The sanitizing interface 1706 may include a translucent material arranged to allow UV light to pass through.

The shape sensors 1702 and 1704 may generate shape data associated with a detected shape of a surface 1712 of the footwear 1710 facing the sanitizing interface 1706. Housing 1700 includes at least one UV light emitter 1714 arranged to emit UV light toward footwear 1710. Housing 1700 further includes a shield panel 1716 positioned between UV light emitter 1714 and sanitizing interface 1706. The shield panel 1716 may include an array of screening cells 1718. Although not shown if FIGS. 17A and 17B, the housing 1700 may include a controller such as controller 1312 arranged to: i) receive the shape data from sensors 1702 and 1704; ii) open a first portion 1720 of the array of screen cells 1718 and close a second portion 1722 of the array of screen cells 1718 in response to the received shape data; and iii) activate UV light emitter 1714 once the array of screen cells are configured in response to the shape data. Housing 1700 may include a proximity sensor 1730 arranged to detect the presence of footwear 1710 when positioned above sanitizing interface 1706, and determine when to start or end the sanitizing process.

In operation, a user places their shoe and/or footwear 1710 (or other object) on the defined sanitization areas and/or sanitizing interface 1706. Proximity sensor 1730, which may be located on or about top surface 1708, senses the presence of footwear 1710 and activates the optical detection sensors 1702 and 1704. All screen cells 1718 are energized and/or opened to permit the optical detection of footwear 1710 located above sanitizing interface and/or shield screen layer 1706. The shape sensor(s) 1702 and 1704 capture the shoe sole and/or bottom surface 1712 of footwear 1720 as two-dimensional shape data and transmit the shape data to controller 1312.

Controller 1312 analyzes and/or processes the shape data and/or information and determines which screening cells 1718 within the array 1716 are to be energized with prescribed voltage to open the cell, or de-energized to close the cell and block the UV-C light from UV emitter 1714. The appropriate cells 1718 within the two-dimensional shape form opposing the bottom surface 1712 of footwear 1710 are energized to permit UV-C light passage and other cells not opposing the bottom surface 1712 are de-energized to safely block UV-C light passage from being transmitted toward the user. The UV-C emitter(s) 1714 is switched on for a predetermined period of time and sanitization of bottom surface 1712 of footwear 1710 occurs. When complete, UV-C emitter(s) 1714 is turned off by controller 1312 and the energized cells 1718 of portion 1720 are de-energized. The sanitizing cycle is complete.

Figure 12:
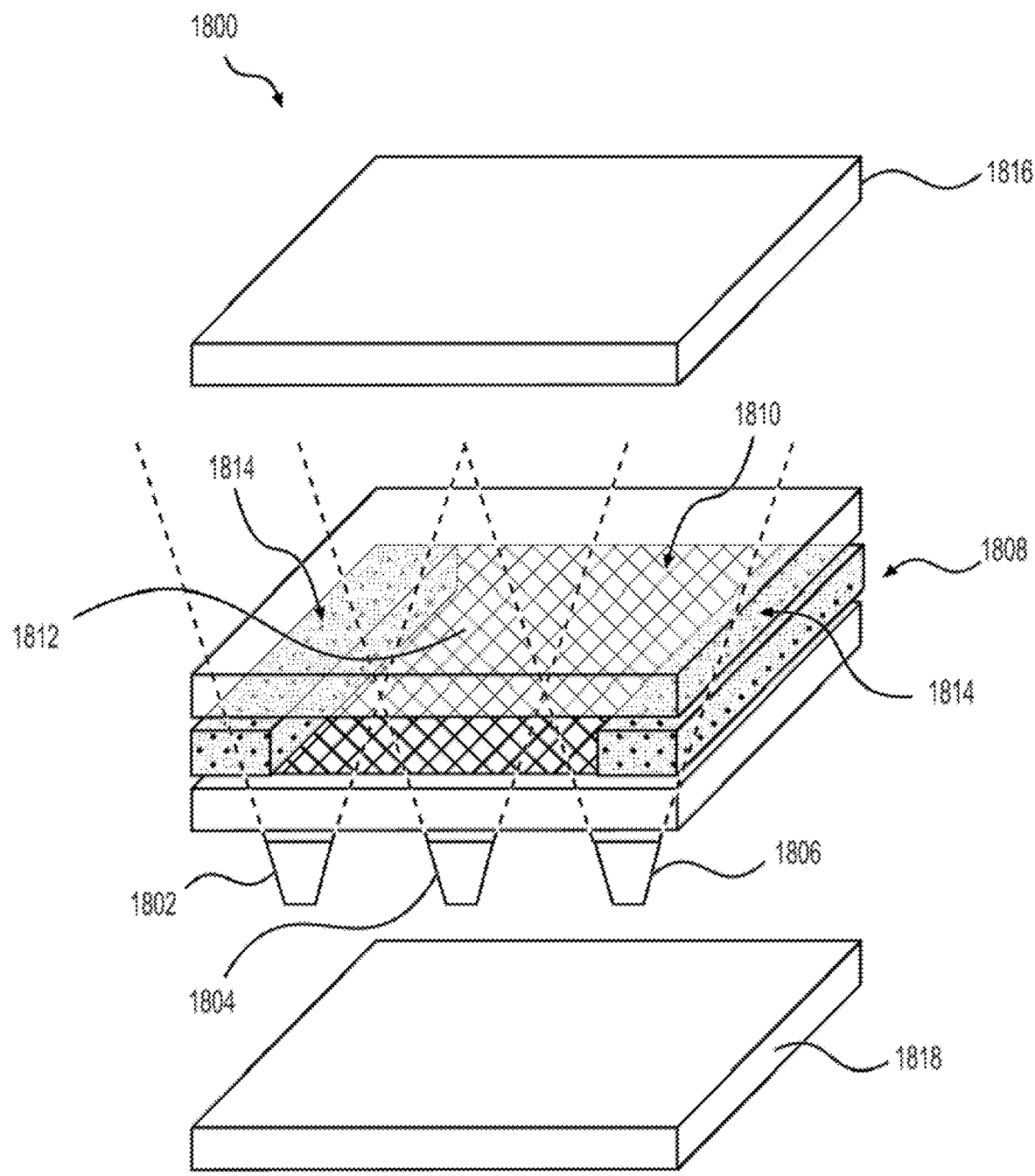
FIG. 12 is an exploded view 1800 of multiple layers of a UV sanitizing device illustrating how the optical sensor(s) 1802, 1804, and 1806 can detect the shape of footwear with a shield layer 1808 including an array of cell and/or shutters 1810. The shield layer 1808 has a portion 1812 of cells that are open to pass through UV light toward the footwear while another portion 1814 of the cells and/or shutters is closed to block portions of UV light not directed toward the footwear from passing through the shield layer 1808.

FIG. 12 is an exploded view 1800 of multiple layers of a UV sanitizing device illustrating how the optical sensor(s) 1802, 1804, and 1806 can detect the shape of footwear. The multiple layers include a shield layer 1808 having an array of cells and/or shutters 1810. The shield layer 1808 has a portion 1812 of cells that are open to pass through UV light toward the footwear while another portion 1814 of the cells and/or shutters is closed to block portions of UV light not directed toward the footwear from passing through the shield layer 1808. The multiple layers may include sanitizing interface and/or surface layer 1816 and a bottom protective layer 1818.

Figure 13:
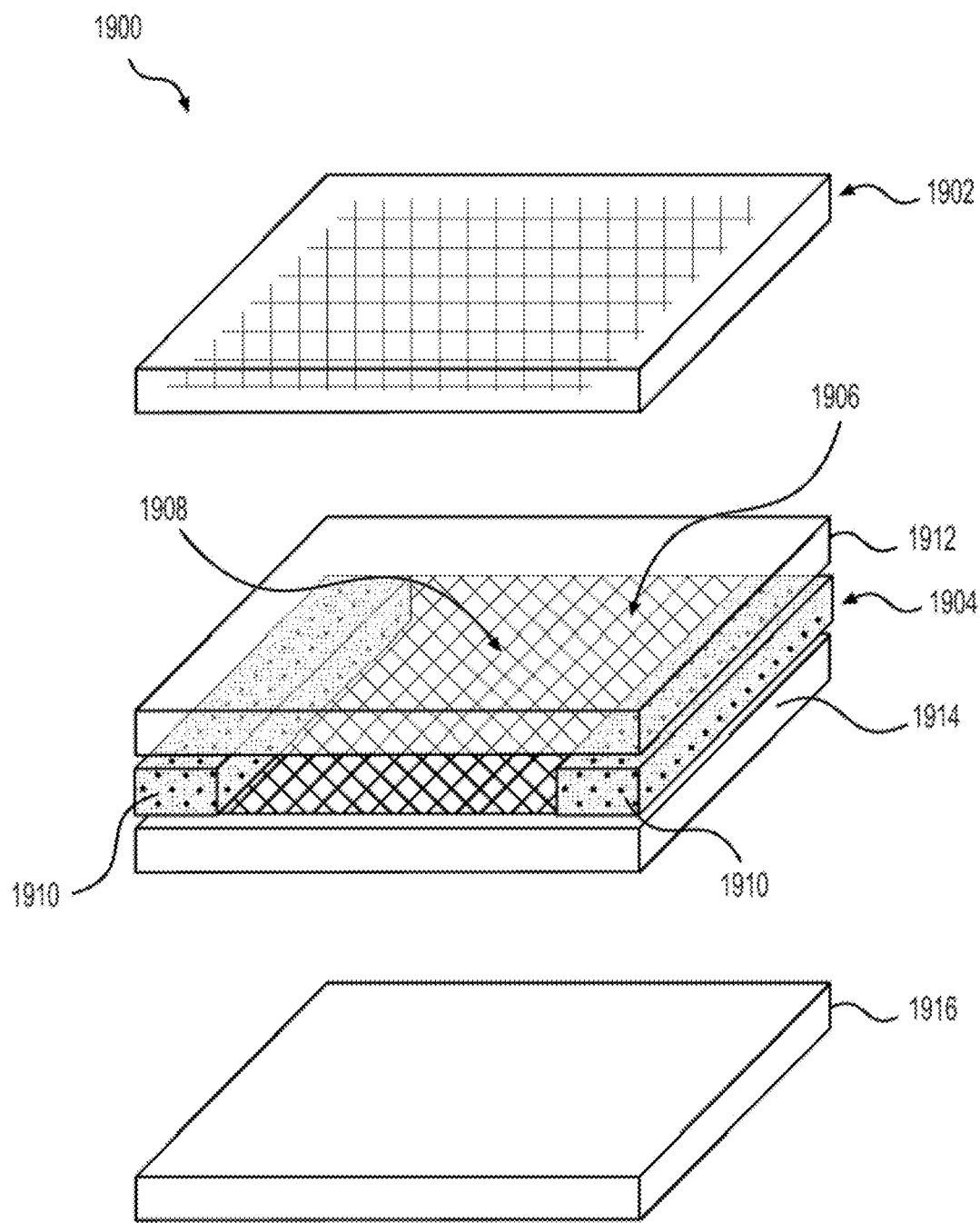
FIG. 13 is an exploded view of multiple layers of a UV sanitizing device illustrating how a mass sensing top layer detects the presence of footwear and a shield layer including an array of shutters with a portion of shutter that are open to pass through UV light toward the detected footwear while another portion of the shutters is closed to block UV light not directed toward the footwear from passing through the shield layer.

FIG. 13 is an exploded view 1900 of multiple layers of a UV sanitizing device illustrating how a mass sensing top layer 1902 detects the presence and/or shape of footwear. The multiple layers include a shield layer 1904 having an array of cells and/or shutters 1906 with a portion 1908 of the cells 1906 that are open to pass through UV light toward the detected footwear while another portion 1910 of the cells 1906 is closed to block UV light not directed toward the footwear from passing through the shield layer 1904. The multiple layers may include layers 1912 and 1914 above and below shield layer 1904 and a bottom protective layer 1916. Mass sensing top layer 1902 may include weight sensing elements, capacitive sensing elements, and/or other elements arranged to detect an object in close proximity to layer 1902.

Figure 14A:
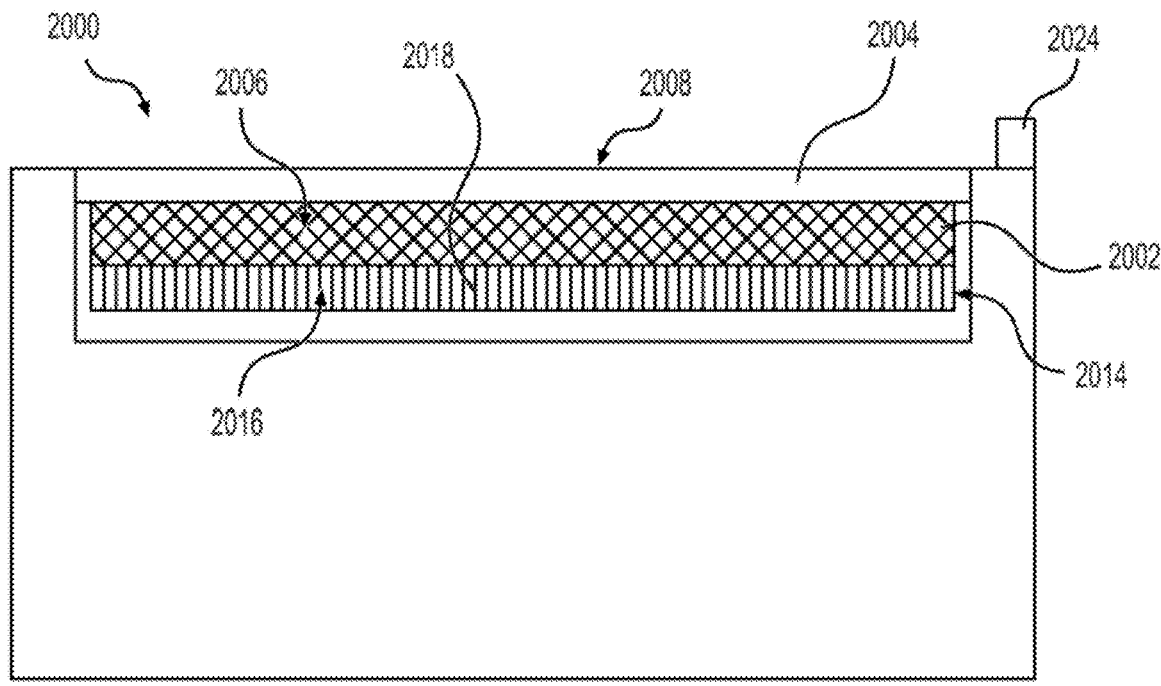
FIG. 14A shows a UV sanitizing housing including a mass sensing layer arranged to detect the presence of an object such as footwear and an UV light emitter layer.

FIG. 14A shows a UV sanitizing housing 2000 including a mass sensing layer 2002 arranged to detect the presence of an object such as footwear 2010. The mass sensing layer 2002 includes at least one mass shape sensor 2006 arranged to detect the 2-dimensional extent of the shape of footwear 2010 that is in close proximity the sanitizing interface 2004. Sanitizing interface 2004 includes a top surface 2008 arranged to support footwear 2010 positioned above the sanitizing interface 2004. The sanitizing interface 2004 may include a translucent material arranged to allow UV light to pass through. The at least one shape sensor 2006 is arranged to generate shape data associated with a detected shape of a surface 2012 of footwear 2010 facing the sanitizing interface 2004. A light emitting panel 2014 includes an array 2016 of UV light emitter cells 2018 arranged to emit UV-C light toward the sanitizing interface and/or top layer 2004. Although not shown in FIGS. 20A and 20B, a controller such as controller 1312 is arranged to: i) receive the shape data and ii) activate a first portion 2020 of the array 2016 of UV light emitter cells 2018 and deactivate a second portion 2022 of the array 2016 of UV light emitter cells 2018 in response to the received shape data.

Figure 14B:
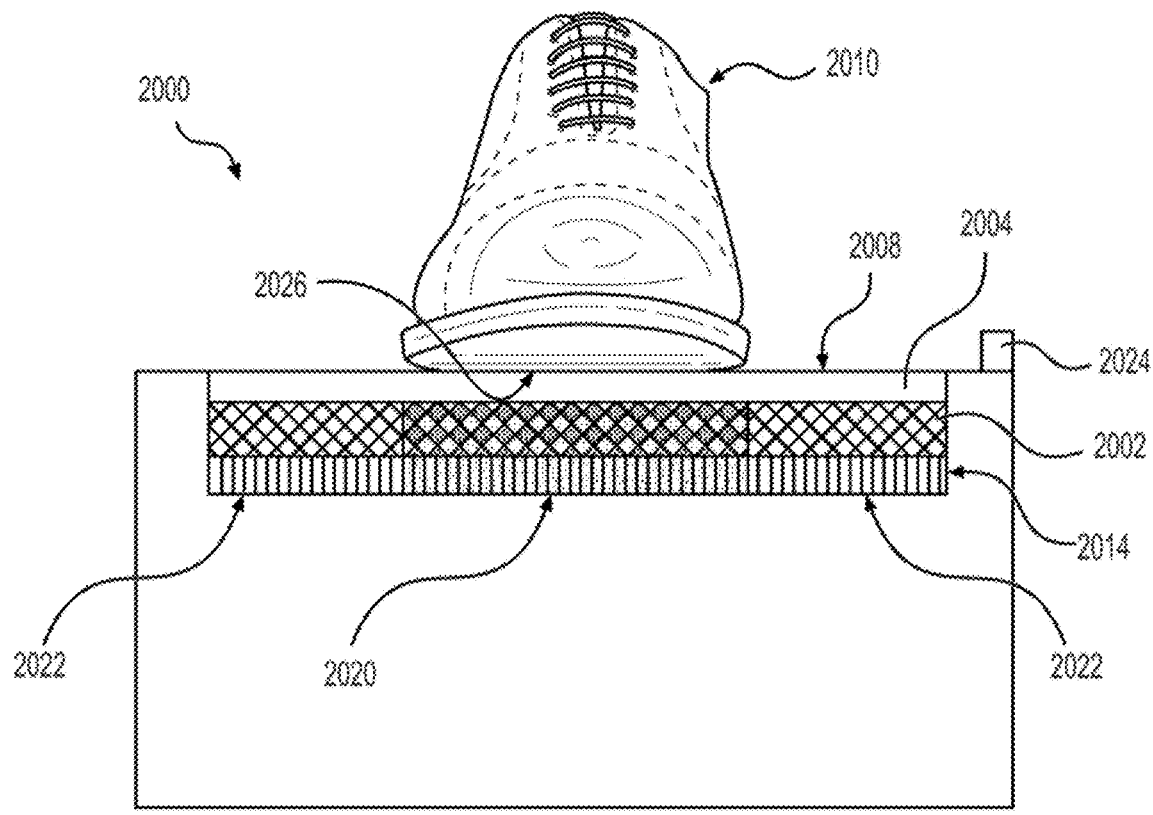
FIG. 14B shows the UV sanitizing housing of FIG. 20A when a first portion of the UV light emitters are emitting light and another portion of the UV light emitters are not emitting UV light.

FIG. 14B shows the UV sanitizing housing 2000 when the UV emitter panel 2014 is emitting UV light while a portion 2020 of the UV light emitter cells 2018 are activated to emit UV light toward footwear 2010 and another portion 2022 of the UV light emitter cells 2018 are deactivated and do not emit UV light. Housing 2000 may include a proximity sensor 2024 arranged to detect the presence of footwear 2010 when positioned above sanitizing interface 2004.

In operation, an optical or mass detection sensor(s) 2006 detects the 2-dimensional extent of the shape of the bottom surface 2026 of footwear 2010 that is in close proximity to the top surface 2008 of sanitizing interface 2004. Controller 1312 interfaces with a memory such as memory 204 which may contain firmware and/or a database that understands the two-dimensional shape of the bottom surface 2026 defined in shape data provided by sensor(s) 2006 and directs portion 2020 of the array 2016 of UV light emitter cells 2018 to be activated while it directs portion 2022 of the array 2016 of UV light emitter cells 2018 to be deactivated. Each of the UV light emitter cells 2018 may include a Micro- or Mini-LED UV-C emitter. The quantity, size, density, and arrangement depend on the application. This system and/or housings 1700 and 2000 can be duplicated one or more times to sanitize multiple surfaces simultaneously. The sensor technology selection may depend upon the sensing needs of the object to be sanitized. The system defined space is scalable up or down by adding sensor and UV-C LED components.

In operation, a user places their footwear 2010 (or other object) on the defined sanitization areas and/or sanitizing interface 2004. Proximity sensor 2024, which may be located on or about surface 2008, senses a presence of a shoe and/or footwear 2010 (or other object) and activates the optical or mass detection sensor(s) 2006. The sensor(s) 2006 capture the shoe sole or bottom surface 2026 (or other object) two-dimensional shape, generate shape data, and transmit the shape data to controller 1312. Controller 1312 processes and/or analyzes the shape data and determines which UV light emitter cells 2018 are to be energized and de-energized. The appropriate UV light emitter cells 2018 within and/or opposing the two-dimensional shape form are energized to emit the sanitizing UV-C light toward the bottom surface 2026 of footwear 2010. When complete, the UV light emitter cells 2018 are turned off by controller 1312 and the sanitizing cycle is complete.

FIGS. 15A and 15B are top down views 2100 and 2150 respectively of a UV sanitizing device showing a portion 2102 of screening cells 2106 that are open and portion 2104 of screening cells 2106 that are closed depending on the size and/or shape of detected footwear or a portion 2102 of UV light emitters that are activated and portion 2104 of UV light emitters 2106 that are not activated depending on the size of the detected footwear.

Figure 16:
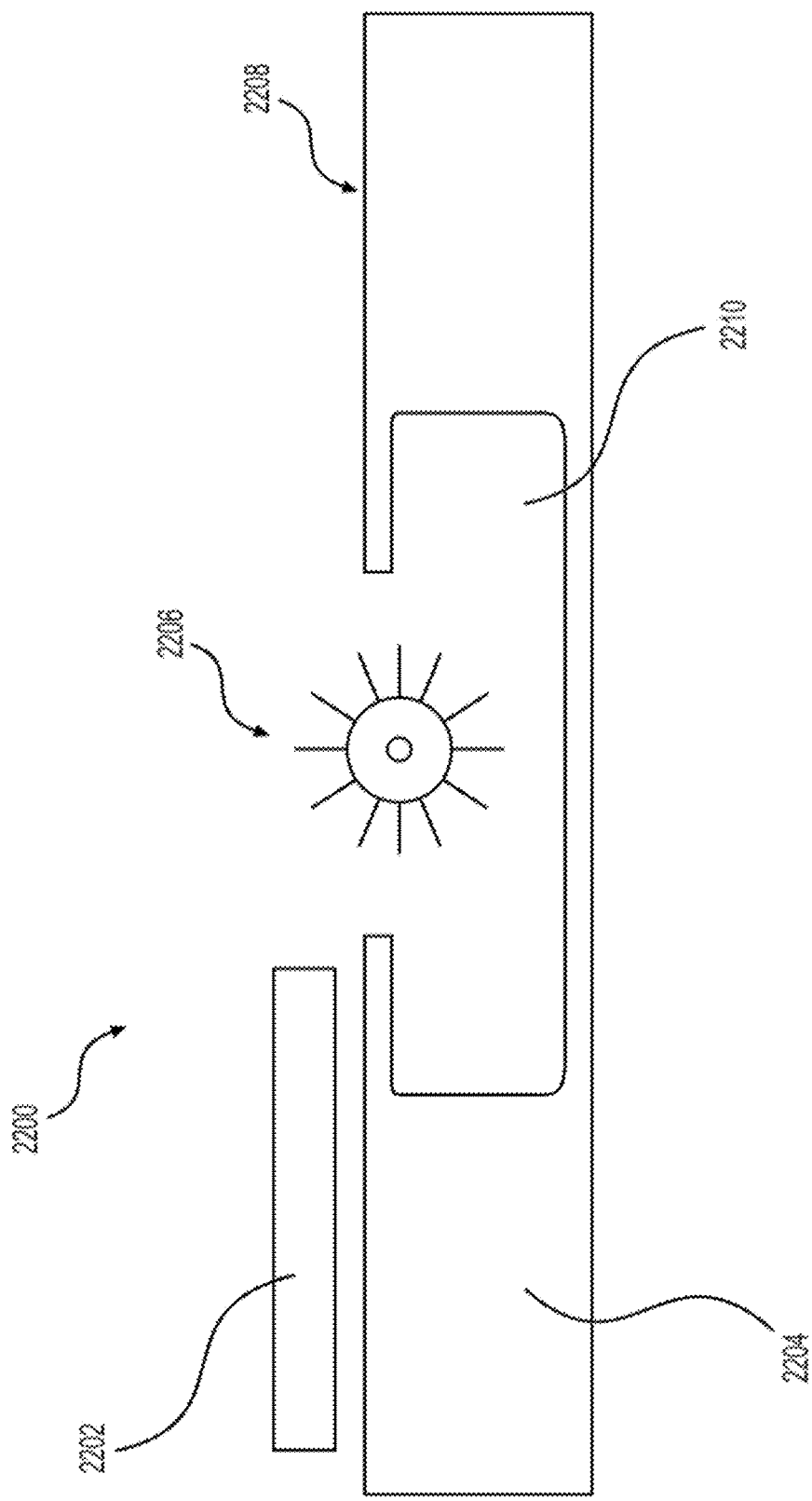
FIG. 16 shows a debris remover arrange to remove debris from a hand-held device.

FIG. 16 shows a debris remover 2200 arrange to remove debris from a hand-held device 2202. The hand-held device 2202 may include a mobile phone. Debris remover includes a housing 2204 having a debris remover unit 2206. The debris remover assembly 2206 may include one or more brushes. As shown in FIG. 16, the assembly 2206 may include one or more rotary brushes arrange to rotate and remove debris from a portion of device 2202 in contact with assembly 2206. A user may move and/or slide device 2202 along the top surface 2208 of debris remover 2200 and over assembly 2206 that, in turn, may rotate and remove debris from device 2202. The debris may be collected in cavity 2210 for later removal. Assembly 2206 may be motor driven. Debris remover 2200 may have one or mare sensor that detect the presence of device 2202 in proximity to debris remover 2200. A controller such as controller 200 or 410 may control activation and/or deactivation of assembly 2206 based on sensor data from the one or more sensors indicating the presence or absence of device 2202 in proximity to the debris remover 2200.

Figure 17:
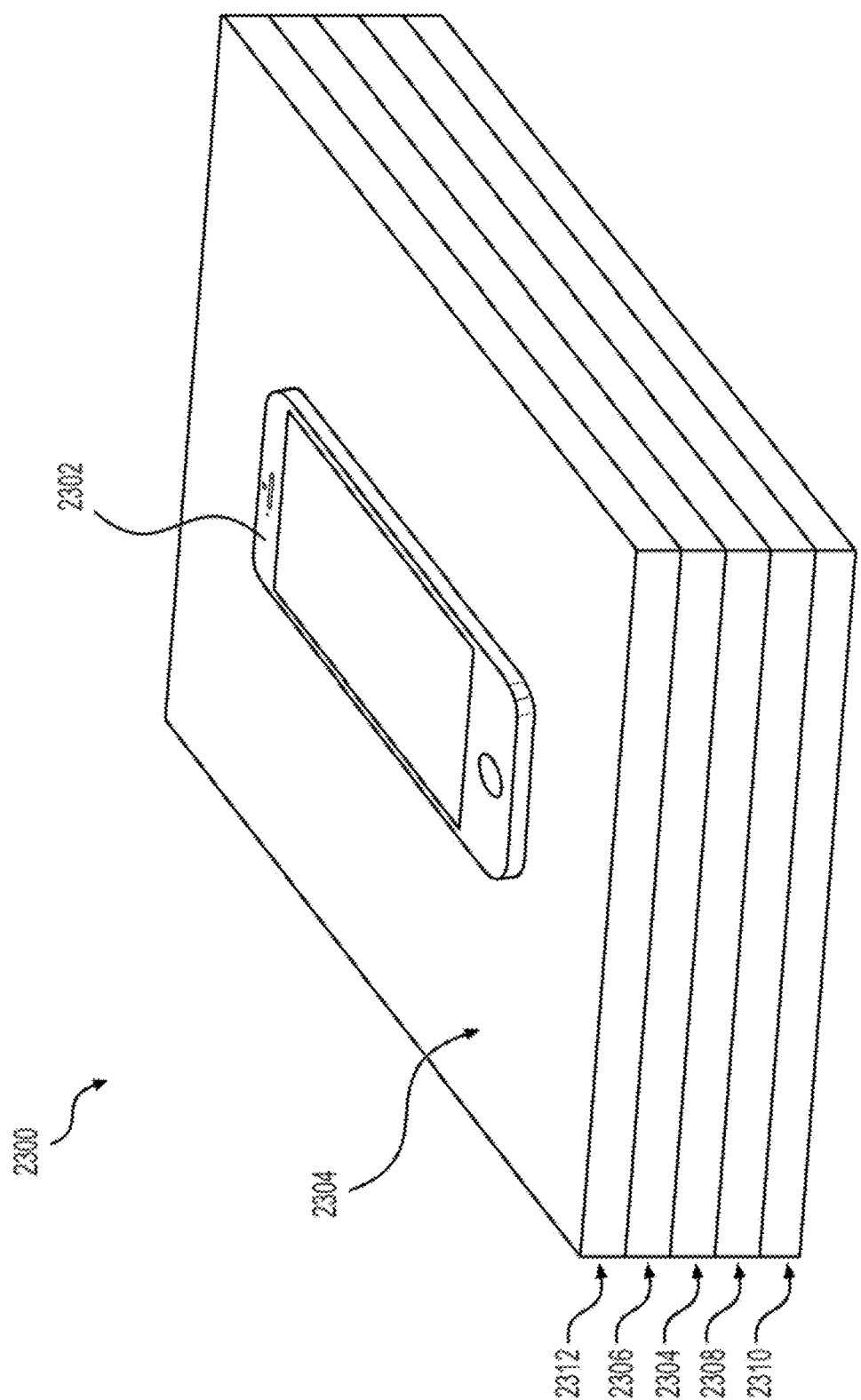
FIG. 17 shows a hand-held device positioned on the top surface of a sanitizer interface.

FIG. 17 shows a sanitizer device 2300 with a hand-held device 2302 positioned on the top surface 2304 of the sanitizer device 2300. The sanitizer device 2300 may include multiple layers such as a shield layer 2304 having an array of cells and/or shutters with a portion of the cells that are open to pass through UV light toward the detected hand-held device 2302 while another portion of the cells is closed to block UV light not directed toward the hand-held device 2302 from passing through the shield layer 2304. The multiple layers may include layers 2306 and 2308 above and below shield layer 2304 and a bottom protective layer 2310. Mass sensing top layer 2312 may include weight sensing elements, capacitive sensing elements, and/or other elements arranged to detect an object such as device 2302 in close proximity to layer 2312. The arrangement and operation of device 2300 is similar to the arrangement and operations of the UV sanitizing device of FIG. 19.

Figure 18:
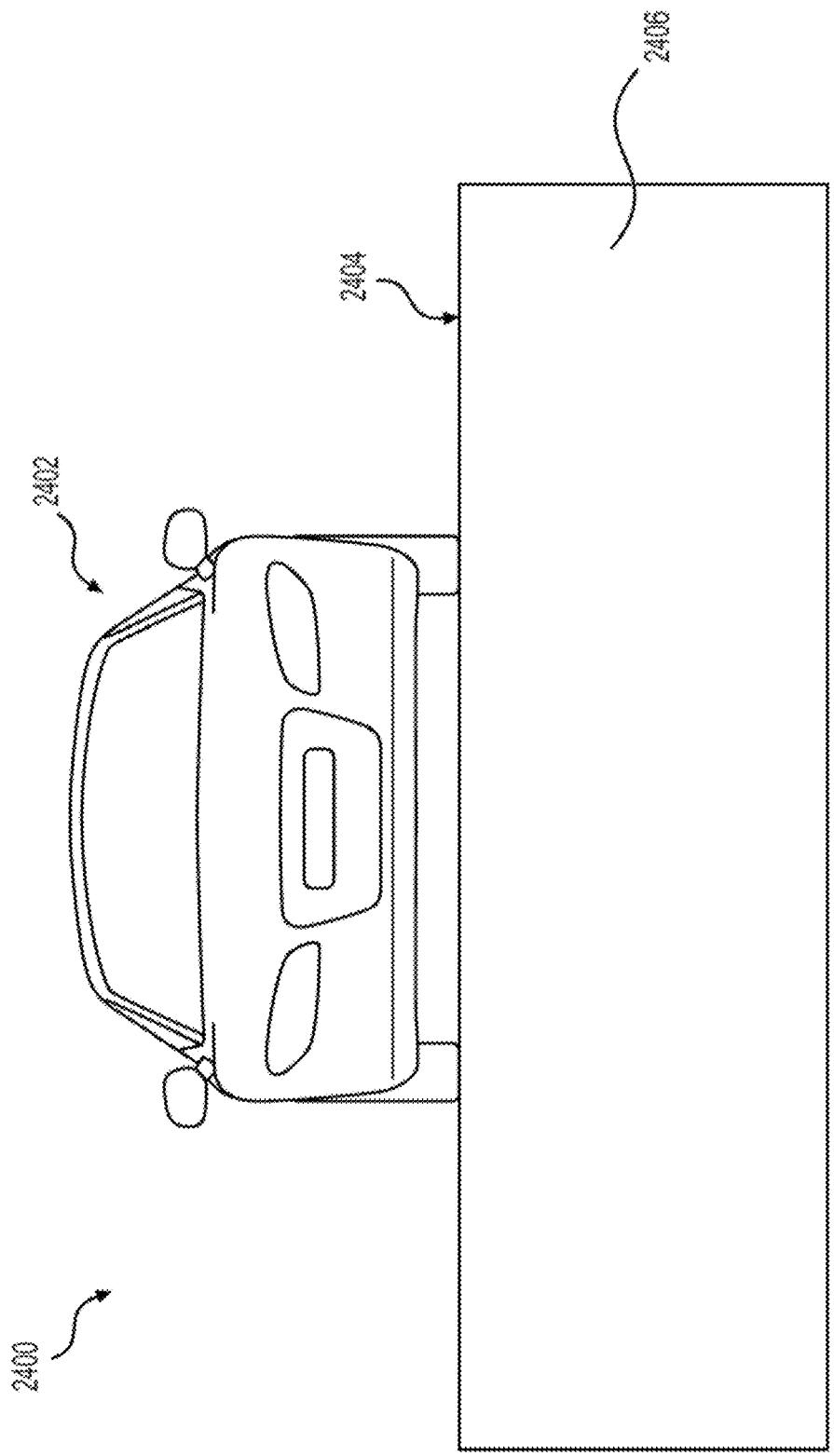
FIG. 18 shows a vehicle positioned above a top surface of a sanitizer interface.

FIG. 18 shows another UV sanitizing system 2400 arrange to sanitize a portion of another device, e.g., a vehicle 2402, positioned above a top surface 2404 of a housing 2406 the sanitizer system 2400. The arrangement and operations of system 2400 may be similar to the arrangement and operations of the UV sanitizer systems of FIGS. 19 and 23. However, the housing 2406 is sized to support and/or provide UV emissions and shield for relatively larger devices such as vehicle 2402.

Figure 19:
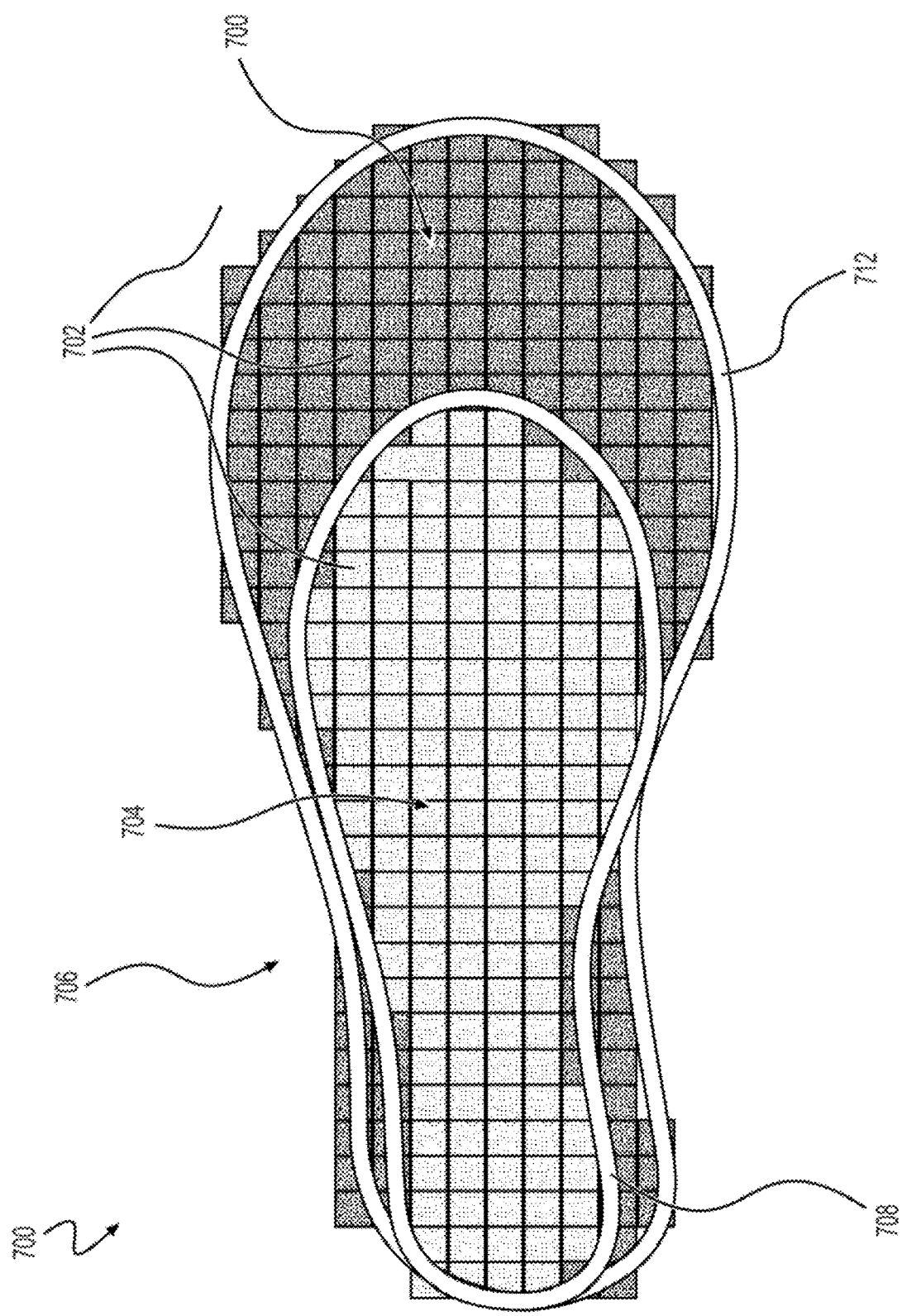
FIG. 19 is another top-down view of a UV sanitizing device showing a first portion of individually-controlled cells that are activated and a second portion of individually-controlled cells that are deactivated depending on the shape of a detected device, e.g., footwear.

FIG. 19 is another top-down view 700 of a UV sanitizing device showing a first portion 704 of individually-controlled cells 702 that are activated and a second portion 706 of individually-controlled cells 702 that are deactivated depending on the shape of a detected device, e.g., footwear 708. FIG. 19 also shows how a third portion 710 of the cells 702 are activated along with portion 704 to cover the shape of a larger footwear 712.

Figure 20:
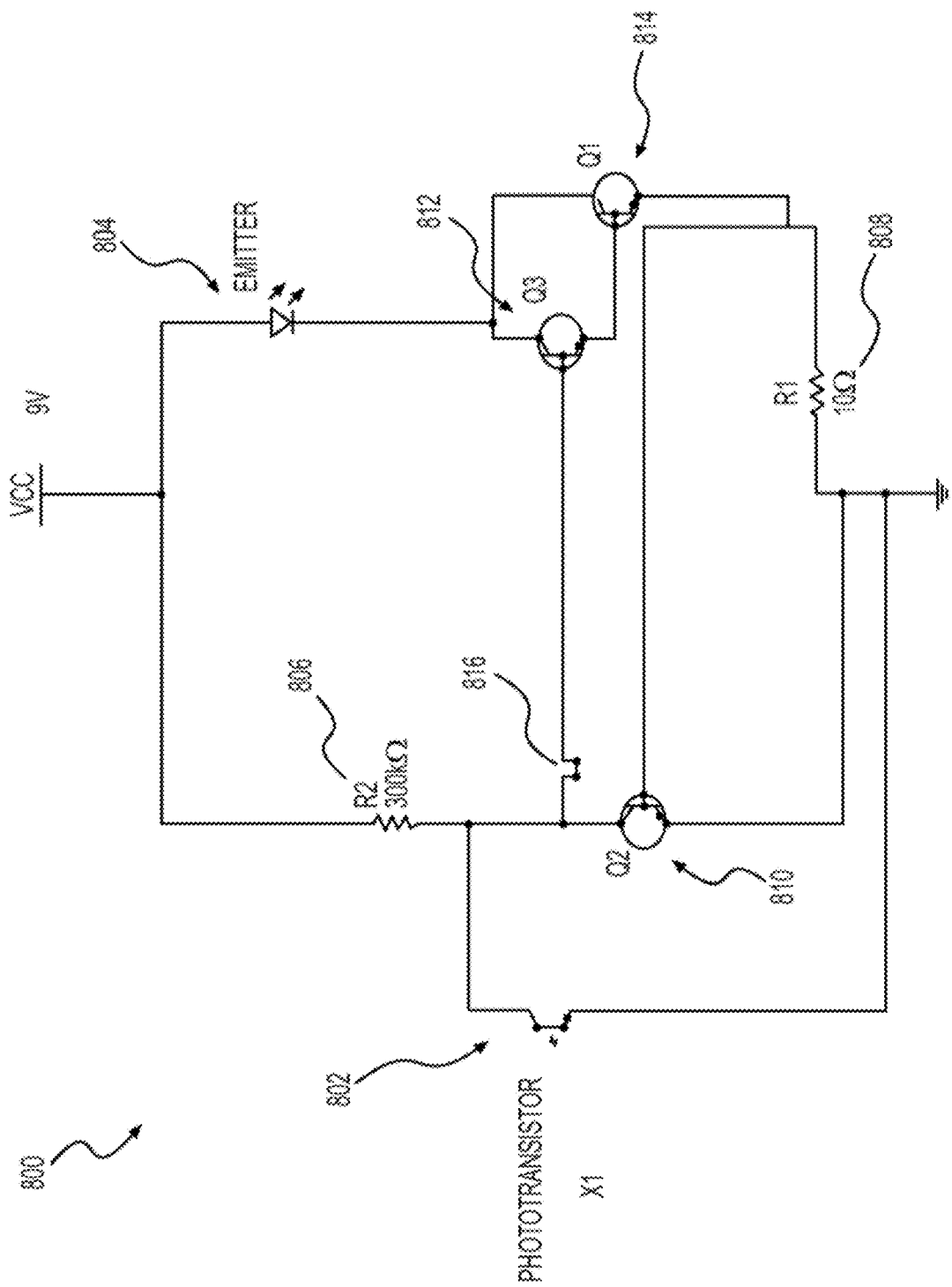
FIG. 20 is a schematic diagram of an exemplary activator circuit including a sensor and UV light emitter of a UV emission interface cell.

FIG. 20 is a schematic diagram of an exemplary activator circuit 800 including a sensor 802 and UV light emitter 804 of a UV emission interface cell such as a cell 702 of FIG. 19. Circuit 800 may include one or more biasing resistors 806 and 808 and/or transistors 810, 812, and 814 that may be configured to set a sensitivity and/or threshold level of light intensity that turns on or off phototransistor 802. For example, phototransistor 802 may be biased to turn off when the light intensity it receives and/or detects drops below a cut-off or threshold level. The cut-off or threshold level may be set to correspond with an expected light intensity when an object is in proximity to, adjacent to, and/or aligned along an axis extending from the phototransistor 802, i.e., the sensor. When an object is not in proximity to or aligned along the axis, the light intensity is likely to be at or above the cut-off level because an object is not blocking light being received by the phototransistor 802.

When the received light intensity at phototransistor 802 is at or above the cut-off level, phototransistor 802 is on and conducting electrical current through resistor 806 which reduces the voltage at the base of transistor 812, causing transistor 812 to shut off, which blocks electrical current through light emitter 804. Thus, light emitter 804 does not emit UV light when the light intensity received by sensor 802 is at or above a light intensity cut-off level. When the received light intensity at phototransistor 802 is below the cut-off level, phototransistor 802 is off and not conducting electrical current through resistor 806, which increases the voltage at the base of transistor 812, causing transistor 812 to turn on and conduct electrical current through light emitter 804. Thus, when an object and/or portion of a device blocks enough light received by phototransistor 802 to cause it to shut off, activator circuit 800 turns on light emitter 804 to emit UV light toward the object and/or portion of a device. While activator circuit 800 includes a phototransistor sensor 802, other types of sensors may be implemented such as, without limitation, a different photo-reactive device (e.g., a photodiode), an acoustic sensor, a sonic sensor, a capacitance sensor, a pressure sensor, a mass sensor, and a magnetic sensor.

The activator circuit 800 may or may not include an activation switch 816 that is controllable manually or automatically from a controller such as controller 410. The controller may open switch 816 to prevent activation of UV light emitter 804 even when phototransistor 802 is in a cut-off state to ensure other conditions are met before the UV light emitter 804 emits UV light. For example, controller 410 may delay activation of a cell or multiple cells 702 for a period of time to ensure an object or device is fully positioned at a sanitizing interface (e.g., 1 sec, 3 seconds, 5 seconds, and so on). Controller 410 may not close switch 816 until a UV sanitizes operation associated with a more complete cleaning and sanitizing operation is ready to be performed. Controller 410 may not close switch 816 until a set number of cells 702 detect that a device is in position to be irradiated with UV light. Controller 410 may not close switch 816 unless a proximity sensor detects the presence of the device when positioned above the sanitizing interface. System 100 and/or 400 may include a safety feature where controller 410 may not close switch 816 or 1016 unless a sensor such as a pressure, weight, and/or mass sensor determines that a sufficiently massive object is positioned above the array of UV light emitters. The sensor may measure the amount of pressure, mass, or weight which controller 410 may compare with a threshold value to determine if switch 816 or 1016 should be closed to enable activation of UV cells. For example, a threshold of 15 lbs may be set such that a weight of at least 15 lbs has to be sensed before switch 816 or 1016 is closed. The value may be set to prevent activation of UV light emitters when a less massive object, such as a child, incidentally steps over or is placed above the UV light emitters.

Figure 21:
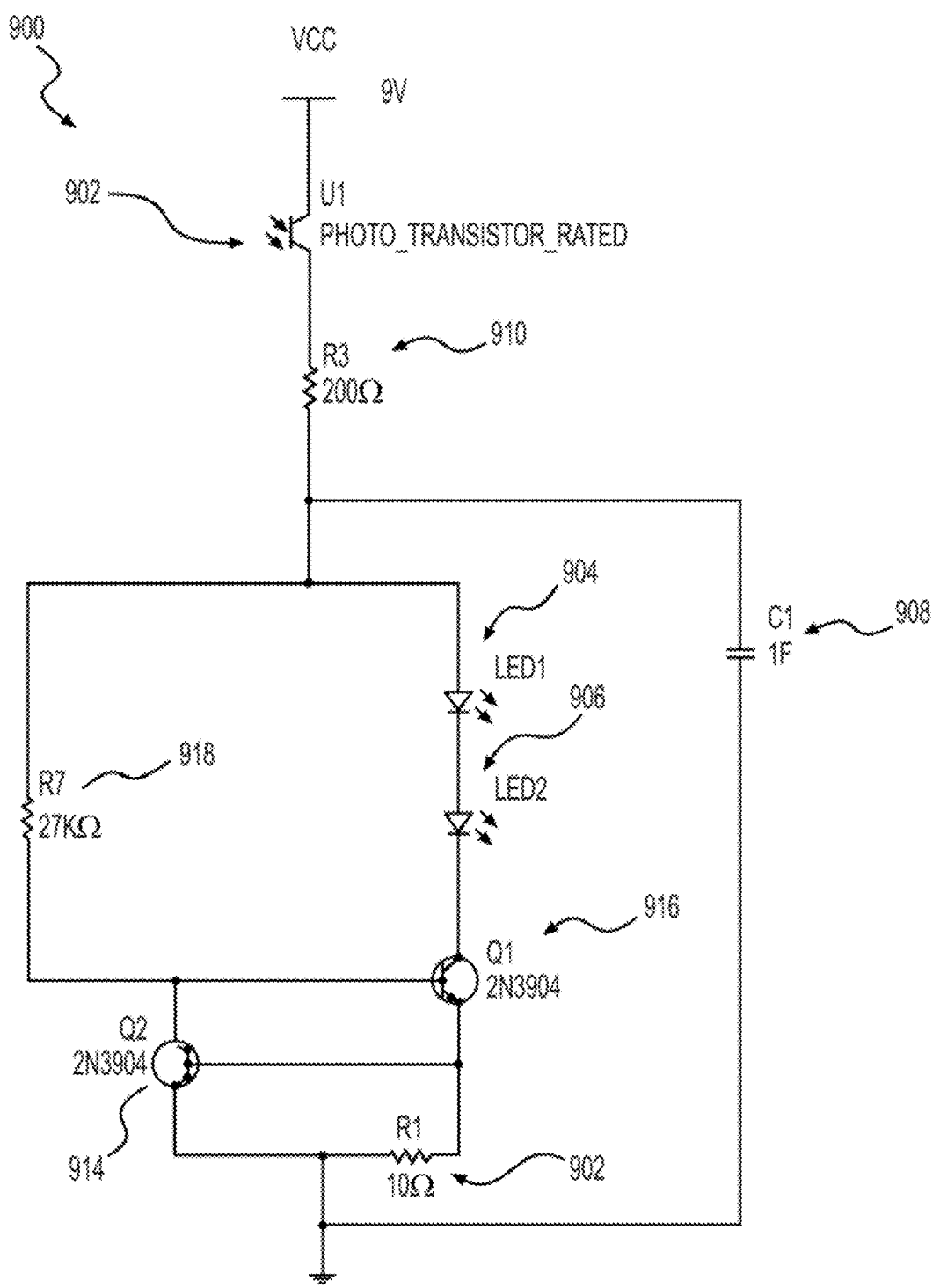
FIG. 21 is a schematic diagram of another exemplary activator circuit including a sensor, UV light emitters, and a super capacitor that is electrically coupled in a parallel with the UV light emitters.

FIG. 21 is a schematic diagram of another exemplary activator circuit 900 including a sensor 902, UV light emitters 904 and 906, and a super and/or discharge capacitor 908 that is electrically coupled in a parallel with the UV light emitters 904 and 906. Circuit 900 may include biasing components such as resistors 910, 912, and 918, and transistors 914 and 916. The biasing components may be configured to set a threshold or cut-off level of light intensity and/or sensitivity at which phototransistor 902, i.e., the sensor, turns off and/or on.

When the received light intensity at phototransistor 902 is at or above the cut-off level, phototransistor 902 is on and conducting electrical current through resistors 910 and 918 which reduces the voltage at the base of transistor 916, causing transistor 916 to shut off, which blocks electrical current through UV light emitters 904 and 906. Thus, light emitters 904 and 906 do not emit UV light when the light intensity received by sensor 902 is at or above a light intensity cut-off level. Also, discharge capacitor 908 is charged to a voltage level just below VCC. When the received light intensity at phototransistor 902 is below the cut-off level, phototransistor 902 is off and not conducting electrical current through resistors 910 and 918, which increases the voltage at the base of transistor 916, causing transistor 916 to turn on and conduct electrical current from discharge capacitor 908 through light emitters 904 and 906. Thus, when an object and/or portion of a device blocks enough light received by phototransistor 902 to cause it to shut off, activator circuit 900 turns on light emitters 904 and 906 to emit UV light toward the object and/or portion of a device. While activator circuit 900 includes a phototransistor sensor 902, other types of sensors may be implemented such as, without limitation, a different photo-reactive device (e.g., a photodiode), an acoustic sensor, a sonic sensor, a capacitance sensor, a pressure sensor, and a magnetic sensor. While activator circuit 900 includes discharge capacitor 908, in other implementations, discharge capacitor 908 may be electrically coupled in parallel with UV light emitters 904 and 906, while being physically located outside of the activator circuit 900 and/or outside of the UV light emission cell.

Figure 22:
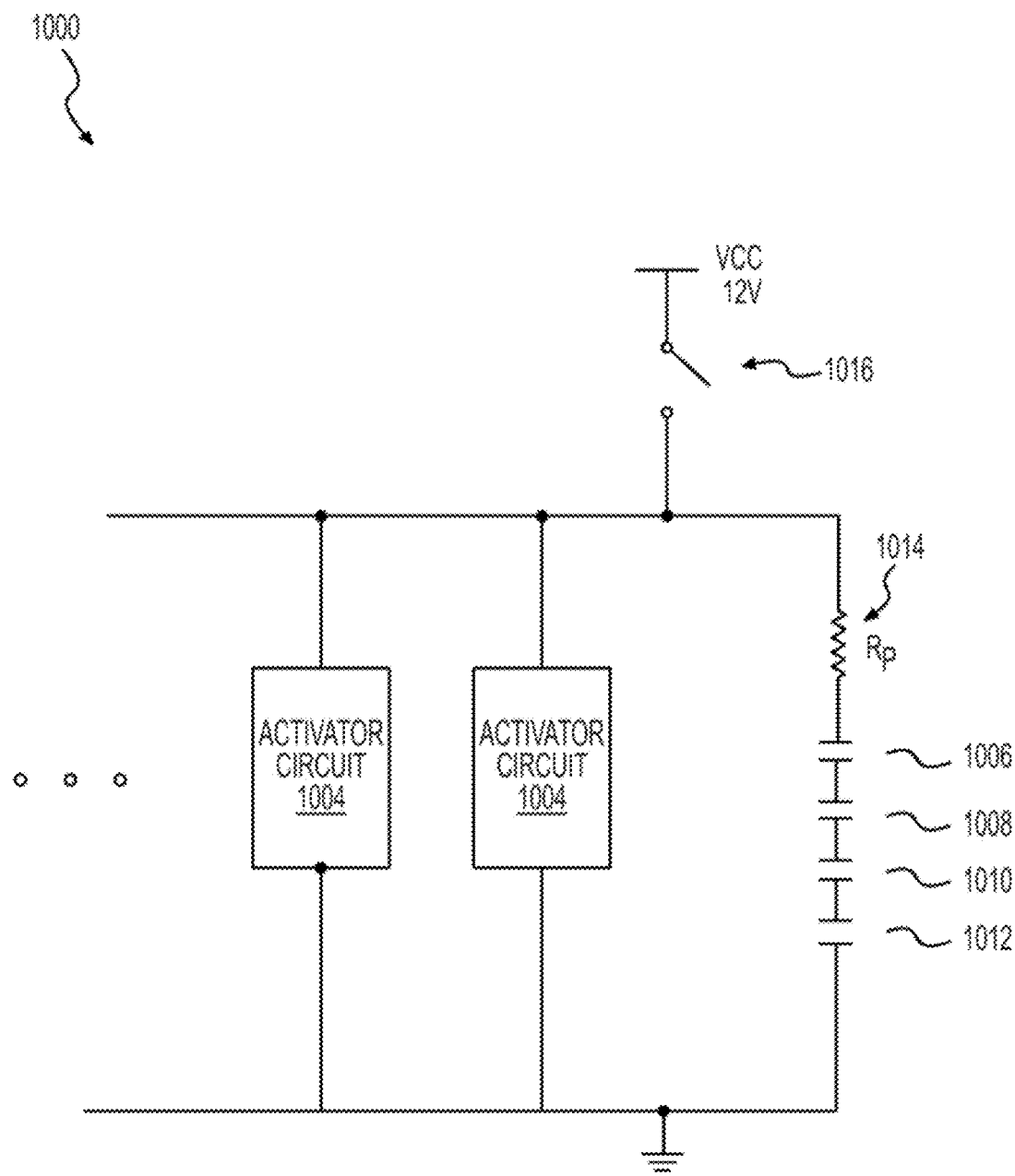
FIG. 22 is a schematic diagram of a multiple UV emission interface cells being electrically coupled in parallel with one or more capacitors.

FIG. 22 is a schematic diagram of a UV light emission circuit 1000 including multiple UV emission interface cells and/or activator circuits 1002 and 1004 that are electrically coupled in parallel with one or more capacitors 1006, 1008, 1010, and 1012. Circuit 1000 may include biasing components such as resistor 1014. Circuit 1000 may include a master control switch 1016 that is configured to prevent activation of the UV light emitters associated with activator circuits 1002 and 1004 when switch 1016 is open, but allow UV light emitters associated with activator circuits 1002 and 1004 to be activated and emit UV light when switch 1016 is closed. Switch 1016 may function in a similar manner as switch 816, but enable manual or automatic control of multiple activator circuits of multiple cells such as cells 702 of FIG. 19. Discharge capacitors 1006, 1008, 1010, and 1012 may be configured to discharge electrical current to drive UV light emitters in circuits 1002 and 1004 while the circuits are activated. Activator circuits 1002 and 1004 may include circuits 800 and/or 900. FIG. 22 also illustrates how any number of cells 702 and/or activator circuits can be arranged in parallel in circuit 1000. In this way, for example, switch 1016 can enable or inhibit the activation of all cells 702 until a sanitizer system is ready to allow the system to emit UV light toward a device. A denser array of cells 702 can increase the accumulated current draw to an undesirable level. Hence, circuits 800, 900, and/or 1000 may include at least one super capacitor which can significantly reduce the amperage demand while UV light emitters are activated. One of ordinary skill understands that various circuits of various configurations may be designed to implement activator circuits that achieve the same or similar functions as described above.

Elements or steps of different implementations described may be combined to form other implementations not specifically set forth previously. Elements or steps may be left out of the systems or processes described previously without adversely affecting their operation or the operation of the system in general. Furthermore, various separate elements or steps may be combined into one or more individual elements or steps to perform the functions described in this specification.

Other implementations not specifically described in this specification are also within the scope of the following claims.

What is claimed is:

1. A UV sanitizing device comprising:
   a sanitizing interface including a top surface arranged to support a device positioned above the sanitizing interface, the sanitizing interface including a translucent material arranged to allow UV light to pass through; and an adjustable UV emission interface, positioned adjacent to the sanitizing interface, arranged to adjustably conform to the shape of a surface of the device facing the sanitizing interface, and arranged to emit the UV light toward the sanitizing interface in the shape of the surface of the device, the adjustable UV emission interface including a plurality of UV emission interface cells such that, when a first portion of the UV emission interface cells is activated and a second portion of the UV emission interface cells is deactivated, the UV emission interface conforms to the shape of the surface of the device;

wherein each cell of the plurality of UV emission interface cells includes a sensor arranged to detect a portion of the surface of the device facing the sanitizing interface.

2. The device of claim 1, wherein each cell of the plurality of UV emission interface cells includes at least one UV light emitter arranged to emit a portion of the UV light toward the device and through the sanitizing interface when activated.

3. The device of claim 2, wherein each cell of the plurality of UV emission interface cells is individually controllable by an activator circuit.

4. The device of claim 3, wherein the activator circuit activates the at least one UV light emitter in response to its respective sensor determining that the portion of the surface of the device facing the sanitizing interface is aligned with its respective sensor along an axis extending from the respective UV emission interface cell toward the portion of the surface of the device facing the sanitizing interface.

5. The device of claim 4, wherein the sensor includes a photo-reactive device.

6. The device of claim 5, wherein the photo-reactive device includes a phototransistor.

7. The device of claim 6, wherein the phototransistor determines that the portion of the surface of the device facing the sanitizing interface is aligned with the phototransistor by detecting a change in light intensity received by the phototransistor.

8. The device of claim 2, wherein the plurality of UV emission interface cells are configured as an array of UV light emitters arranged to selectively activate the first portion of the UV emission interface cells and deactivate the second portion of the UV emission interface cells to emit the UV light toward the surface of first device.

9. The device of claim 2, wherein the at least one UV light emitter in each of the plurality of the UV emission interface cells includes an LED emitter.

10. The device of claim 1, wherein the sensor includes at least one of a photo-reactive device, an acoustic sensor, a sonic sensor, a capacitance sensor, a pressure sensor, and a magnetic sensor.

* * * * *